(12) United States Patent
Wen et al.

(10) Patent No.: US 7,914,819 B1
(45) Date of Patent: Mar. 29, 2011

(54) POLYSACCHARIDE-BASED BIOMATERIALS

(75) Inventors: Xuejun Wen, Mount Pleasant, SC (US); Yongzhi Qiu, Charleston, SC (US)

(73) Assignee: Clemson University Research Foundation, Anderson, SC (US)

( * ) Notice: Subject to any disclaimer, the term of this patent is extended or adjusted under 35 U.S.C. 154(b) by 623 days.

(21) Appl. No.: 11/875,436

(22) Filed: Oct. 19, 2007

Related U.S. Application Data

(60) Provisional application No. 60/852,755, filed on Oct. 19, 2006.

(51) Int. Cl.
*A61K 31/715* (2006.01)
*A61K 38/00* (2006.01)
*C07K 14/00* (2006.01)

(52) U.S. Cl. .................. 424/488; 514/2; 530/300

(58) Field of Classification Search ............... None
See application file for complete search history.

(56) References Cited

U.S. PATENT DOCUMENTS

| | | | |
|---|---|---|---|
| 5,482,717 | A | 1/1996 | Fues et al. |
| 6,322,797 | B1 | 11/2001 | Mao et al. |
| 153,528 | A1 | 8/2003 | Levinson |
| 6,773,723 | B1 * | 8/2004 | Spiro et al. ............... 424/488 |
| 2003/0232746 | A1 * | 12/2003 | Lamberti et al. ............ 514/2 |

OTHER PUBLICATIONS

Article—M. Riminucci and P. Bianco; Building bone tissue: matrices and scaffolds in physiology and biotechnology; 15 pgs.; Oct. 12, 2006, Brazilian Journal of Medical and Biological Research.

Article—Johnna S. Temenoff and Antonios G. Mikos; Injectable biodegradable materials for orthopedic tissue engineering; 8 pgs, Biomaterials 21 (2000) 2405-2412.

Article—(abstract only) Amit S. Mistry and Antonios G. Mikos; Tissue Engineering Strategies for Bon Regeneration; 2 pgs; 2005; Advances in Biochemical Engineering/Biotechnology.

Article—K. Rezwan, Q.Z. Chen, J.J. Blaker, Aldo Roberto Boccaccini; Biodegradable and bioactive porous polymer/inorganic composite scaffolds for bone tissue engineering; 18 pgs.;Dec. 6, 2005; Biomaterials 27 (2006) 3413-3431.

Article—J.K. Francis Suh and Howard W.T. Matthew; Application of chitosan-based polysaccharide biomaterials in cartilage tissue engineering; a review; 10 pgs.; Biomaterials 21 (2000) 2589-2598.

Article—Yang-Jo Seol, Jue-Yeon Lee, Yoon-Jeong Park, Yong-Moo Lee, Young-Ku, In-Chul Rhyu, Seung-Jin Lee, Soo-Boo Han & Chong-Pyoung Chung; Chitosan sponges as tissue engineering scaffolds for bone formation; Biotechnology Letters 26: 1037-1041, 2004.

Article—Bin-Hong Tsai, Chih-Hsiu Lin, Jui-Che Lin; Synthesis and property evaluations of photocrosslinkable chitosan derivative and its photocopolymerization with poly(ethylene glycol); Journal of Applied Polymer Science, vol. 100, 1794-1801 (2006).

Article—Dana L. Nettles, M.S., Steven H. Elder, Ph.D., and Jerome A. Gilbert, Ph.D.; Potential use of chitosan as a cell scaffold material for cartilage tissue engineering, 9 pgs.; Tissue Engineering, vol. 8, No. 6, 2002.

Article—Mohamed E. I. Badawy, Entsar I. Rabea, Tina M. Rogge, Christian V. Stevens, Guy Smagghe, Walter Steurbaut, and Monica Hofte; Synthesis and fungicidal activity of new N, O-Acyl chitosan derivatives; 6 pgs; Biomacromolecules 2004, 5, 589-595.

Article—Karen J. L. Burg, Scott Porter, and James F. Kellam; Biomaterial developments for bone tissue engineering; 13 pgs., Biomaterials 21 (2000) 2347-2359.

\* cited by examiner

*Primary Examiner* — Anand U Desai
(74) *Attorney, Agent, or Firm* — Dority & Manning, P.A.

(57) ABSTRACT

Disclosed are a series of kneadable, pliable polymers for use in forming compositions that can be used as bone wax or as a cellular scaffold. Polymers can include a polysaccharide backbone and can be biocompatible and thrombogenic. In addition, the compositions can be osteoconductive as well as biodegradable. The disclosed compositions can be used to help control bleeding from bone surfaces as well as to promote bone regeneration and fusion. The compositions can inhibit the growth of microorganisms in implantation sites and can be loaded with additional bioactive agents to further promote healing and infection prevention.

24 Claims, 21 Drawing Sheets

Figure 1 – Prior Art

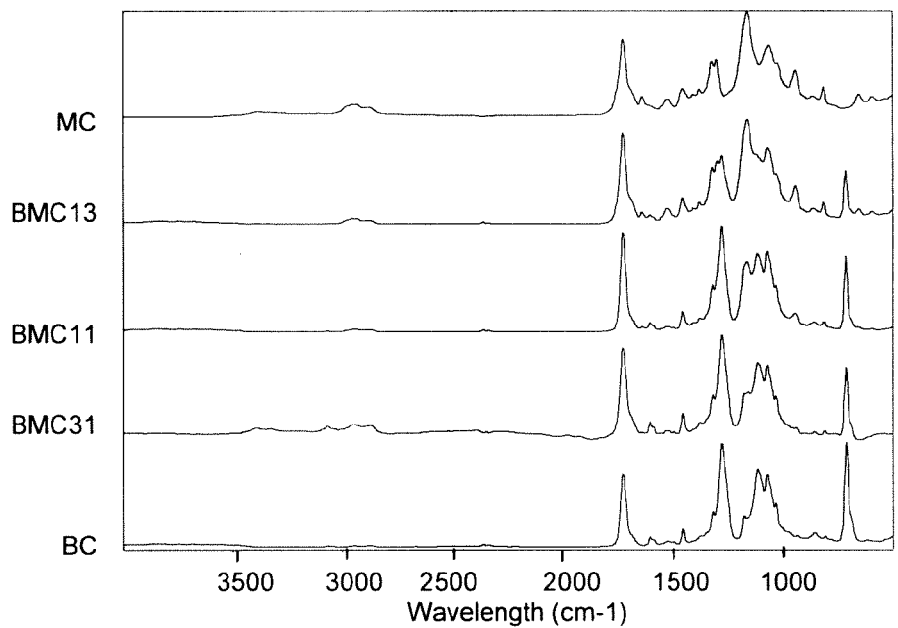
Figure 2
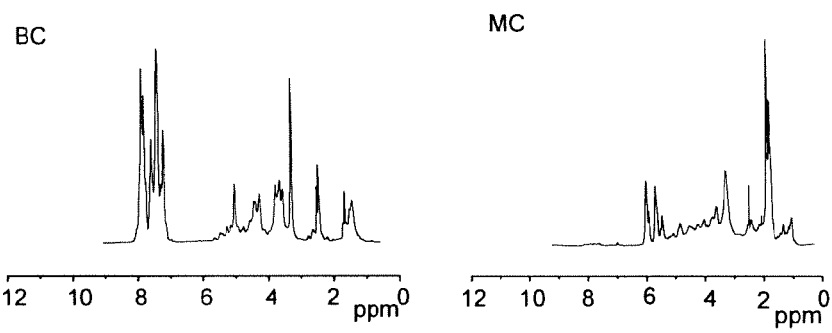
Fig. 3A    Fig. 3B
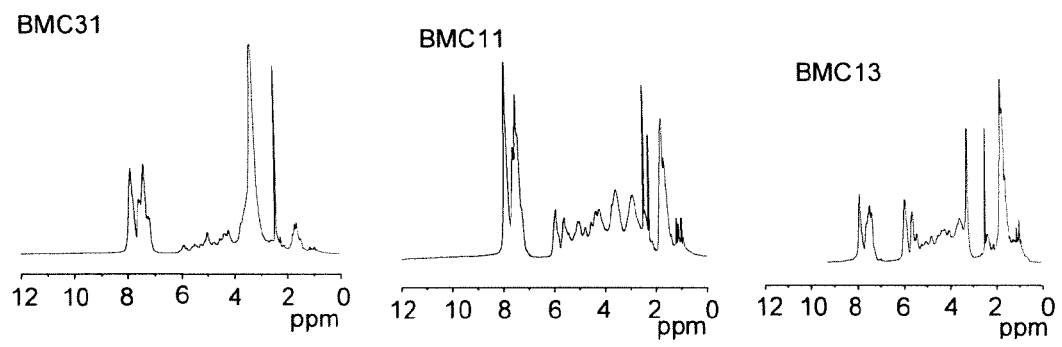
Fig. 3C    Fig. 3D    Fig. 3E
Figure 3

13A  13B 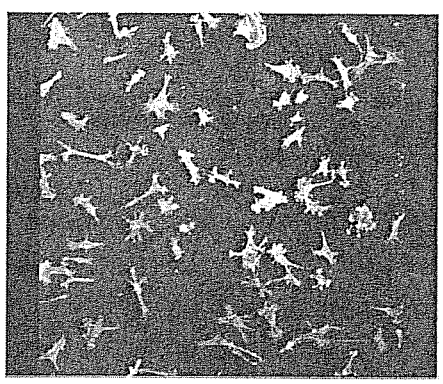
13C 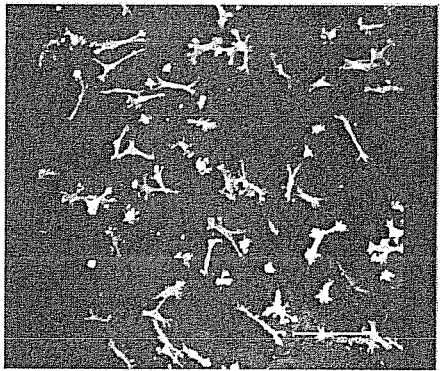 13D 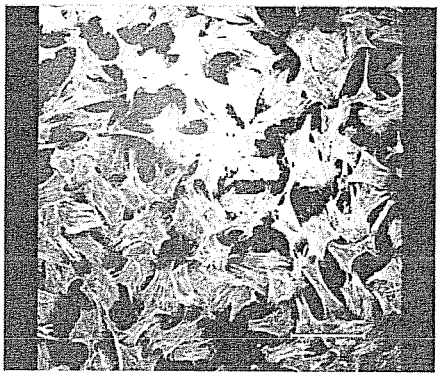
Figure 13

Figure 16
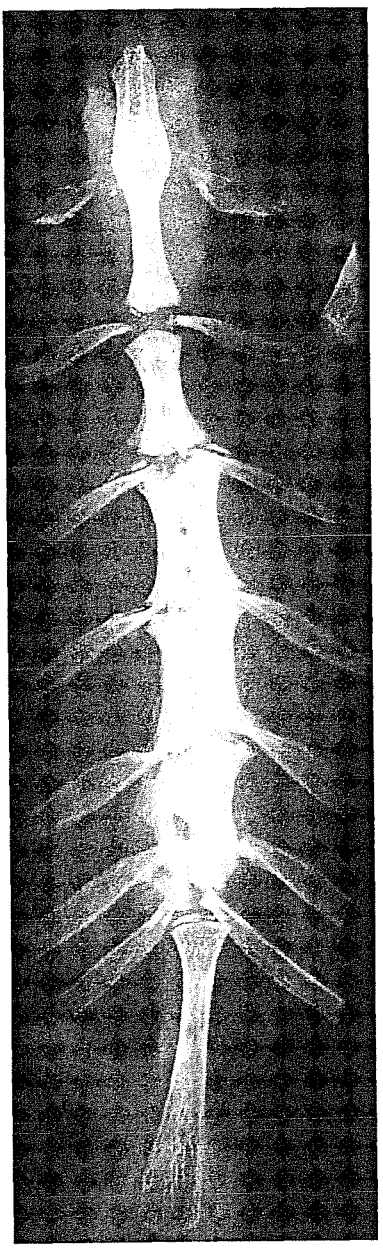
Fig. 16A
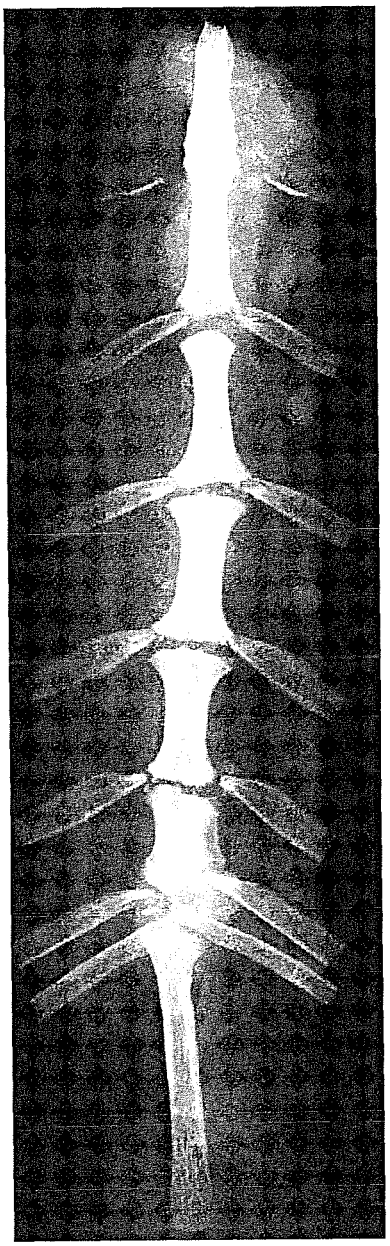
Fig. 16B

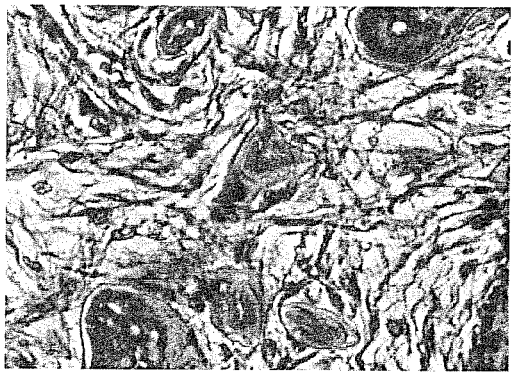 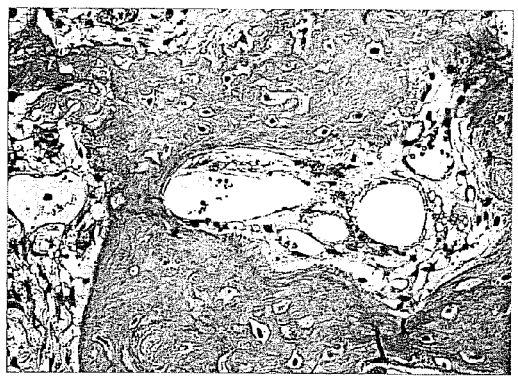
Fig. 17A  Fig. 17B
Figure 17
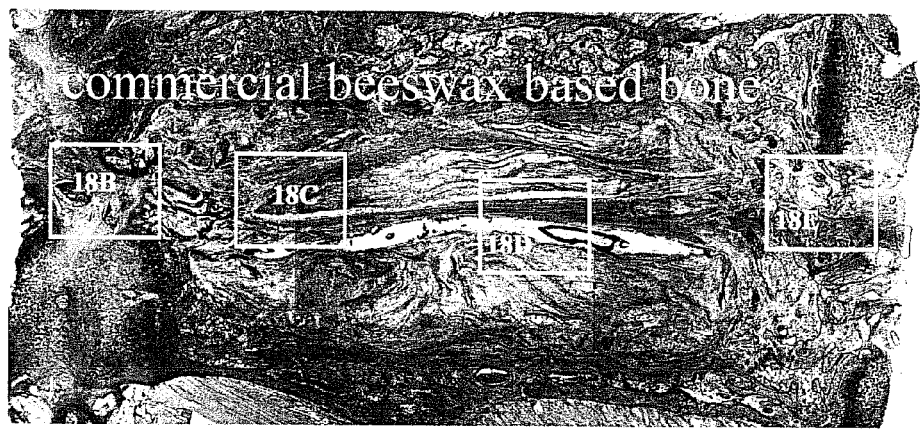
Figure 18A

NB → Nondegradable Bonewax

IC → Intact cartilage between each

FS → Fibrous scar tissue

BT → Bone tissue

NB → Nondegradable Bonewax

FS → Fibrous scar tissue

NB ●→  Nondegradable Bonewax

FS →  Fibrous scar tissue

NB ●→  Nondegradable Bonewax

IC →  Intact cartilage between each

FS →  Fibrous scar tissue

BT →  Bone tissue

M → Marrow

BT → Bone tissue

M → Marrow

BT → Bone tissue

IC → Intact Cartilage between each sternum

M → Marrow

BT → Bone tissue

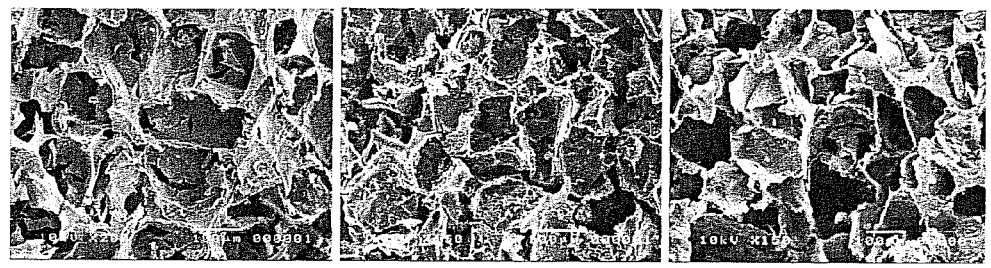
Fig. 20A    Fig. 20B    Fig. 20C
Figure 20
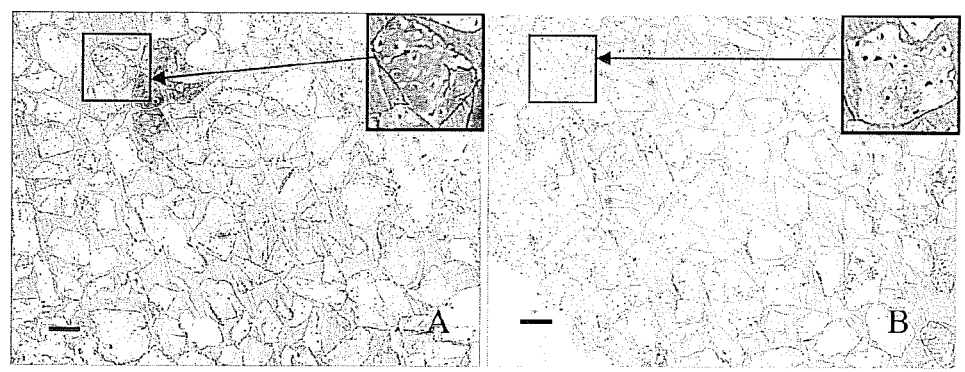
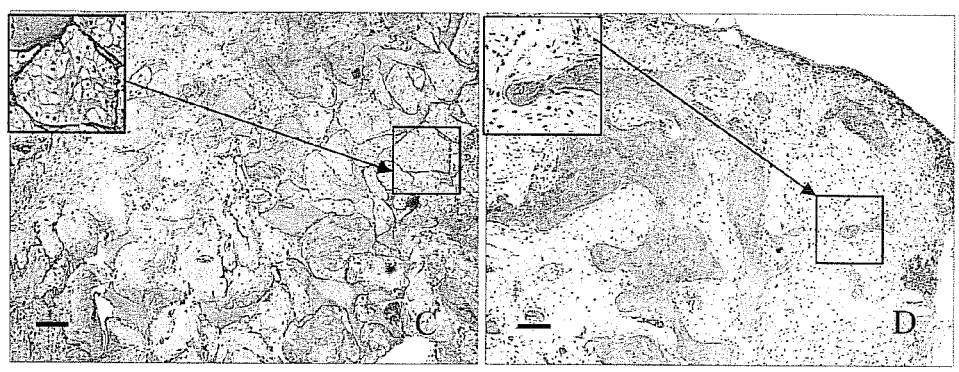
Figure 21

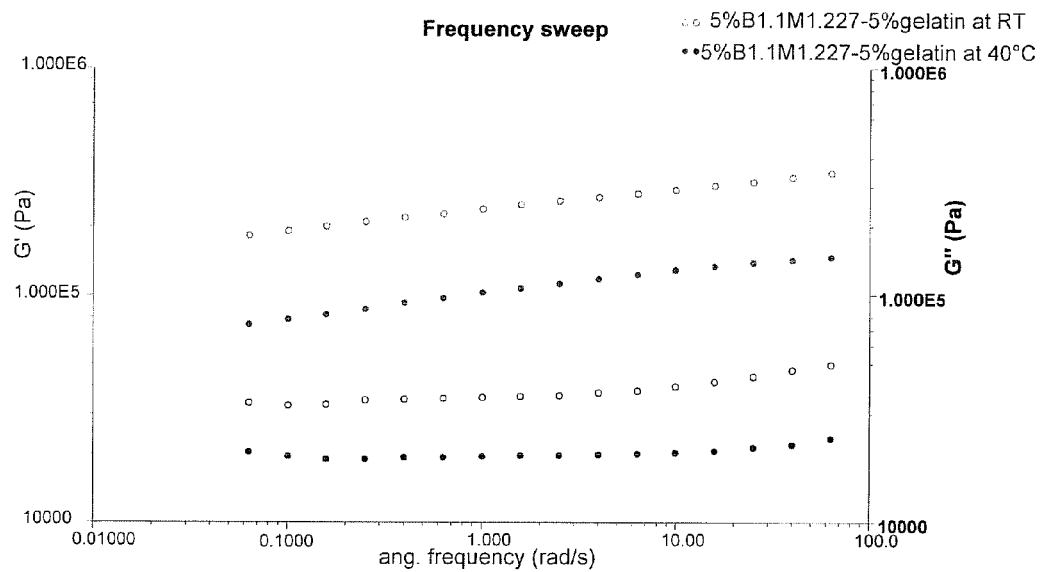
Fig. 24A
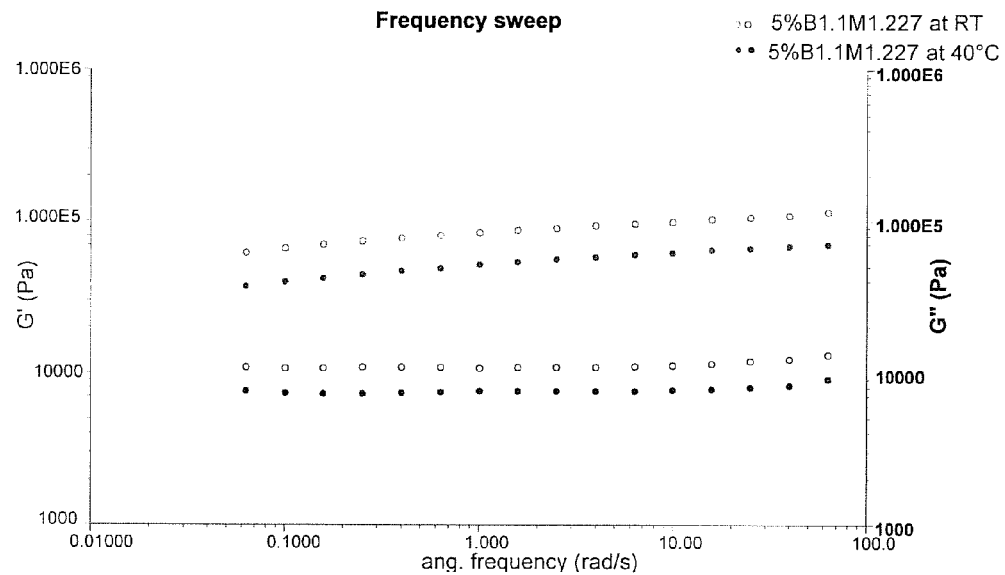
Fig. 24B
Figure 24

US 7,914,819 B1

POLYSACCHARIDE-BASED BIOMATERIALS

CROSS REFERENCE TO RELATED APPLICATION

The present application claims filing benefit of United States provisional patent application having the Ser. No. 60/852,755 filed on Oct. 19, 2006, which is incorporated by reference herein in its entirety.

BACKGROUND OF THE INVENTION

Conventional bone wax is a sterile beeswax preparation that can optionally include softening agents in combination with the beeswax to improve pliability. Conventional bone wax is commonly used as a hemostatic material to control local bleeding.

While conventional beeswax-based bone wax can be formed so as to exhibit acceptable pliability and adhesive qualities, problems exist with these materials. For instance, beeswax-based bone wax inhibits bone regeneration as well as bone fusion, as can be seen with reference to FIG. 1, which illustrates a transverse section of a sternal specimen two weeks following a sternotomy. The conventional bone wax, marked as W on the figure, can be seen at the non-union location of the specimen. As can be seen, conventional beeswax-based bone wax is not suitable for use in regions where osseous regeneration and/or fusion is desired. In addition, beeswax-based bone wax is not degradable and use can lead to foreign body reaction by the recipient. Also, studies have shown that there can be infection following application of beeswax-based bone wax. This is believed to be due at least in part to an impairment of the ability of cancellous bone to clear infectious agents such as bacteria due to the presence of the bone wax.

Accordingly, alternatives to and additives for conventional beeswax-based bone wax have been sought. For example, U.S. Pat. No. 5,482,717 to Fues, et al. describes a resorbable bone wax product produced using glycerol or glycerol partial esters that also includes salts of glycolic acid and/or lactic acid added to the wax. U.S. Patent Application Publication 2003/0153528 to Levinson describes a hemostatic cationic biopolymer of glucosamine that can be formulated together with a sterile beeswax preparation.

While the above illustrate improvements in the art, room for additional improvement exists.

SUMMARY

Subject matter disclosed herein includes biodegradable compositions that can include a crosslinked, osteogenic, polymeric matrix, methods for forming the compositions and methods of application for the compositions. For instance, compositions as disclosed herein can be utilized as scaffolds for tissue regeneration, bone hemostatic materials, or in other applications described in more detail below.

In general, a crosslinked polymeric matrix of a composition can include a polysaccharide backbone that has been derivatized with functional groups. In one preferred embodiment, the polysaccharide can be a chitosan. A first functional group grafted to the polysaccharide backbone can crosslink the polymer. For example, a photocurable crosslinking functional group can be grafted to the polysaccharide. A second functional group can improve the solubility of the polymer in a solvent, and, depending upon the characteristics of this second functional group, the second functional group can improve the solubility of the polymer in either an organic or an aqueous solvent, as desired.

The polysaccharide backbone can be derivatized with additional functional groups, in certain embodiments.

Following or prior to crosslinking, additives can be incorporated into the matrix. For instance, an additive can be incorporated into the matrix to provide porosity to the formed composition. According to this embodiment, an interconnected porosity can be developed upon removal of the additive following crosslinking of the polymer. Other additives can include biologically active materials such as structural and/or functional proteins as well as non-proteinaceous biologically active materials.

BRIEF DESCRIPTION OF THE FIGURES

A full and enabling disclosure of the present invention, including the best mode thereof, to one of ordinary skill in the art, is set forth more particularly in the remainder of the specification, including reference to the accompanying figures, in which:

FIG. 2 illustrates Fourier transform infrared (FTIR) spectroscopy results of exemplary compositions formed as described herein;

FIGS. 3A-3E illustrate the nuclear magnetic resonance (NMR) spectra of each of the compositions of FIG. 2;

FIG. 13 illustrates the morphology of osteoblast cultures following 7 days culturing on compositions as described herein;

FIG. 16 compares X-ray radiography images of a first sternal specimen (FIG. 16A) to which a beeswax-based bone wax has been applied and a second sternal specimen (FIG. 16B) to which a bone wax composition as herein disclosed has been applied;

FIG. 17 compares the in vivo osteoconductivity of a composition as herein disclosed (FIG. 17B) as compared to that of a beeswax-based composition (FIG. 17A);

FIG. 18A is an image of a section of the specimen of FIG. 16A including a beeswax-based bone wax implantation zone;

FIGS. 18B-18E are images of portions of FIG. 18a;

FIGS. 20A-20C illustrate the morphology of porous scaffolds formed as described herein;

FIGS. 21A-21D are histological pictures of four different scaffolds formed as described herein;

FIGS. 24A and 24B illustrate results of rheology studies of two different photocured chitosan compositions formed as described herein;

(FIG. 25A) and at 37° C. (FIG. 25B) for two photocured chitosan compositions as described herein;

DETAILED DESCRIPTION

Figure 1:
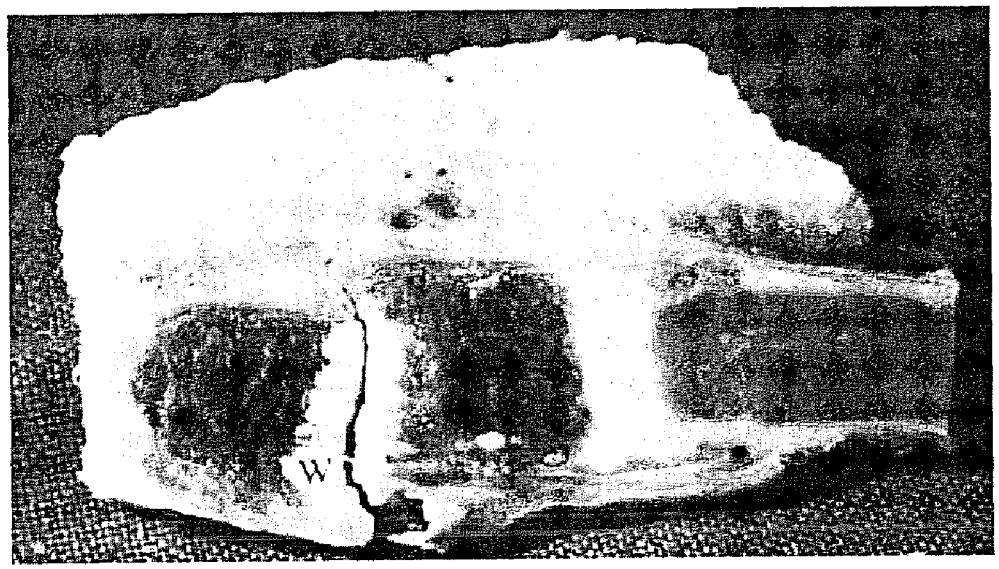
FIG. 1 is a photograph of a transverse section of a sternal specimen two weeks following a sternotomy including application of a conventional beeswax-based bone wax.

Reference will now be made in detail to various embodiments of the disclosed subject matter, one or more examples of which are set forth below. Each embodiment is provided by way of explanation, not limitation of the disclosed subject matter.

In general, the present disclosure is related to compositions that can advantageously be utilized in one embodiment as a bone wax and in another embodiment as a scaffold for tissue regeneration in vitro and/or in vivo. For instance, disclosed materials can be formed with suitably pliability and kneadability so as to be formed, shaped, and located as desired during use. In addition, the disclosed materials can be thrombogenic, and as such can be utilized to control bleeding at implant sites.

Disclosed compositions can exhibit improved characteristics as compared to conventional beeswax-based bone wax. For example, disclosed compositions can be osteogenic and can in some embodiments also be osteoinductive. Accordingly, a composition as herein disclosed can be utilized where bone fusion and/or regeneration is desired. Moreover, disclosed compositions can be degradable. As such, a composition as described herein can degrade over time with the breakdown products being naturally cleared from the area of application so as to prevent problems associated with long-term presence of implanted materials, such as are known to occur with beeswax-based bone wax.

The disclosed compositions can also be antimicrobial, and can inhibit growth of microorganisms at and near the implant site as well as in a cell culture developed on disclosed scaffolds. Accordingly, a composition as herein disclosed can prevent infections such as osteomyelitis from developing at or near an implant site. In one embodiment, a composition can be loaded with biologically active additives such as antibiotics, drugs, or other useful additives. For example, a composition can include an antibiotic and the ability of a composition to inhibit infection at the implant sight can be further enhanced through the addition of the additive.

A useful polymer for forming a hemostatic, osteogenic composition as herein disclosed can include a polysaccharide backbone. For example, a polymer of the composition can include a polysaccharide backbone derived from a biocompatible glucosaminoglycan, cellulose, chitin, chitosan, dextran, starch, xylan, hyaluronic acid, and the like.

In one embodiment, a polysaccharide backbone can be derived from a chitosan. Chitosan is a linear polysaccharide composed of randomly distributed β-(1-4)-linked D-glucosamine (deacetylated unit) and N-acetyl-D-glucosamine (acetylated unit).

A starting polysaccharide, such as chitosan, can be derivatized with desirable functionality to form a biocompatible composition. For example, in one embodiment a polysaccharide can be derivatized with a first functional group so as to provide crosslink sites to the polymer, and a second functional group to improve solubility of the polymer. For instance, the polysaccharide can be provided with improved organic solubility through the addition of an appropriate functionality via an acyl chloride such as propionyl chloride, butyryl chloride, valeryl chloride, hexanoyl chloride, haptanyl chloride, decanoyl chloride, and the like, or an aromatic chloride such as benzoyl chloride, cinnamoyl chloride, coumaricyl chloride, and the like.

In one preferred embodiment, the polysaccharide can be derivatized with a functional group to provide photocuring capability to the polymer. For instance, an acrylate, methacrylate or the like can be grafted to the polymer backbone to provide photocurable crosslink functionality to the polymer. For instance, an acyl chloride containing a carbon-carbon double bond can be utilized including, without limitation, acryloyl chloride, methacryloyl chloride, cinnamoyl chloride, coumaricyl chloride, arachidonoyl chloride, itaconyl chloride, and so on. The incorporation of photocurable groups can help in one embodiment to regulate the mechanical properties, biodegradation rate and swelling ratio for the formed networks.

According to one embodiment, a polysaccharide starting material (e.g., chitosan) can be derivatized through reaction with multiple acyl chlorides, and the ratio between different acyl chlorides can be adjusted to provide particular solubility and crosslink characteristics to the product polymer. For instance, benzoyl chloride and/or cinnamoyl chloride can be added to an acyl chloride mixture to improve the solubility of the formed polymer in organic solvent, and methacryloyl chloride, acryloyl chloride and/or cinnamoyl chloride can be used to provide photocurability to the product. Other photocurable materials as may be grafted onto the polysaccharide backbone can include, without limitation, PEG-dimethacrylate, PCL-dimethacrylate, PCL-di (LDI-methacrylate), PLA-dimethacrylate PLA-di (LDI-dimethacrylate), and the like.

One method of forming a chitosan-based biocompatible polymeric matrix that is soluble in an organic solvent and photocurable can be illustrated as follows:

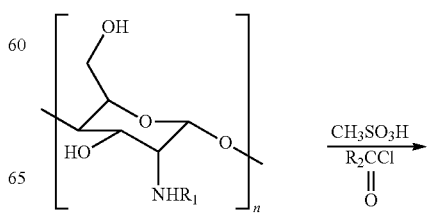

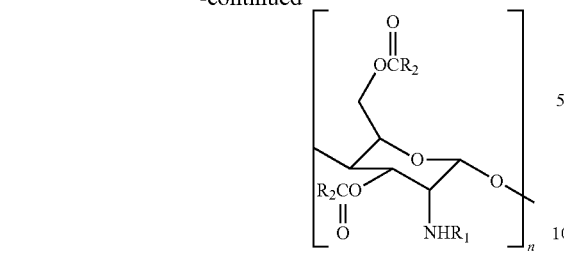

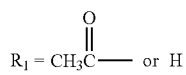

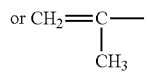

Through adjusting the feeding ratio of the raw components, the content of photocurable groups on the backbone can be controlled. Moreover, as the crosslink density of the product polymer can be controlled according to the quantity of reactants included in the formation process, the product polymer can be formed with desirable characteristics for multiple applications. For example, in one embodiment, a photocurable, organically soluble chitosan can include a relatively high crosslink density so as to provide, for example, a three dimensional scaffolding matrix that can support living cells. The polymeric matrix can be incorporated with bioactive molecules, such as proteins, growth factors, drugs, and the like, and as discussed further below, that can support living cells encapsulated within the matrix. In other applications, the compositions can be utilized as a bone wax, or other augmentation for bone defects, that can be photocured in situ. As such, disclosed materials can be utilized in one embodiment in minimally invasive surgical procedures.

Light curable polymers are showing great potential in overcoming some current obstacles in bone repair. For instance, utilizing stereolithography, photocurable polymers as disclosed herein can be fabricated into scaffolds with desired topography for repairing bone defects in irregular shapes. The capability to undergo photopolymerization upon light exposure can provide many advantages compared to chemical polymerization, including a high polymerization rate that overcomes the oxygen inhibition and solvent effects in normal polymerization, good temporal and spatial control and resolution, ambient temperature operation and low energy consumption. Moreover, light-curable materials may be used for computer-aided fabrication through rapid prototyping which allows fabricating scaffolds with customized shape and reproducible microarchitecture on a large scale.

It should be understood that disclosed polymers and polymeric systems are not limited to photocurable, organically soluble materials described above. Disclosed polymers can include additional or alternative functionalities, in other embodiments. For instance, disclosed polysaccharide-based polymers do not require photocuring capability, and in other embodiments, disclosed materials can be cured according to temperature, time, pH, or the like.

According to one embodiment, polymers can be grafted with additional functionalities, in addition to cross-linkers and/or solubility functionalities as discussed above. For example, in one embodiment, a polymer as disclosed herein can include the following general structure:

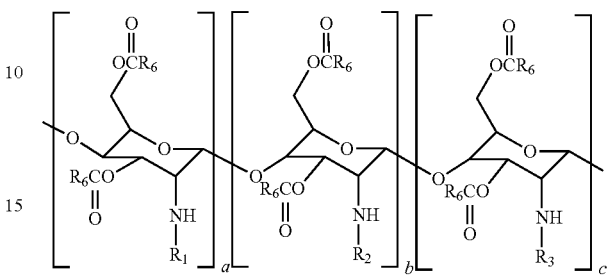

wherein:
R1=CO—NH—$R_4$—NH—CO—O—$(CH_2CH_2O)_n$—CO—NH—$R_4$—NH—CO—$R_5$
R2=CO—NH—R4-NH—CO—O—R7-C—NH—R4-NH—CO—R5

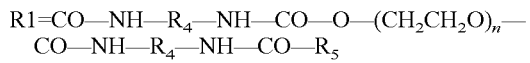

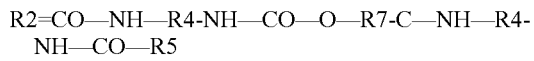

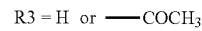 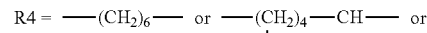

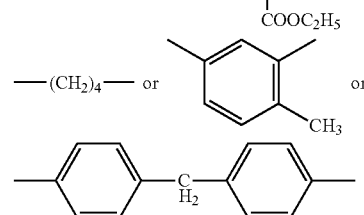

R5=$C_nH_{2n+1}O$

 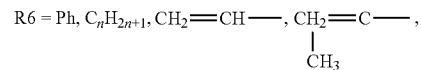

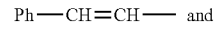

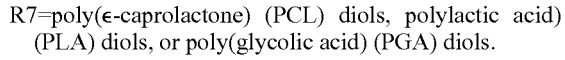

R7=poly(ε-caprolactone) (PCL) diols, polylactic acid) (PLA) diols, or poly(glycolic acid) (PGA) diols.

One method for forming a polymer according to such an embodiment can include initial modification of the starting polysaccharide, e.g., chitosan, to improve solubility in an organic solvent, and optionally to also include photo-crosslinkable groups on the backbone, as described above. For instance, an R6 group can be introduced into the chitosan backbone by reaction with hydroxyl groups according to known methods. Suitable R6 groups can be saturated or unsaturated. In one embodiment, unsaturated R6 groups can be introduced into the backbone. According to this embodiment, the polymer can be capable of undergoing photocrosslinking. Following addition of R6 groups to the backbone, the polymer can be dissolvable in general organic solvents.

During a second step of the formation process, one or more molecules with more than one hydroxyl group, such as diols (e.g., PCL diols, PLA diols, PGA diols, glycerol, polyethylene glycol (PEG) or polyethylene oxide (PEO), or mixtures thereof), triols and/or other polyols can be endcapped with diisocyanate according to any suitable method as is known in the art, examples of which are described in more detail below, such that the products include cyanate groups at both ends. Any diisocyanate can be utilized including, for example, L-lysine diisocyanate (LDI), methylene diphenyl 4-4' diisocyanate (MDI), 1,4 butane diisocyanate (BDI), toluene-2,4 diisocyanate (TDI), 1,6 hexamethylene diisocyanate (HDI), and the like.

These materials can then be further reacted with an alcohol to obtain oligomer/polymer chains, the majority of which can include a cyanate group at only one end of the chain. Depending upon specific reaction conditions, however, an amount of this material can maintain cyanate groups at both ends of the chains. When this is the case, i.e., a portion of the reactants including cyanate groups at both chain ends. The final polysaccharide-based polymer can be somewhat cross-linked via these groups. The cross-link density of the final polymer can thus be controlled through control of this amount, i.e., the amount of oligomer/polymer chains formed at this step that include cyanate groups at both ends of the chain.

The modified chitosan can be reacted with the cyanate-terminated chains to form the polysaccharide-based polymer. Specifically, the terminal cyanate groups can preferentially react with the amino groups of the backbone to graft the degradable chains pendant to the backbone.

Through predetermination and control of the ratios of the blocks of the polymer (e.g., a:b:c ratio in the above scheme) the polymer properties can be controlled. For instance, the degradation rate, the crosslinking density, the thermal properties, the density, and the like, of the polymer can be controlled through the predetermination of the pendant groups as well as the relative ratios of each block on the final polymer. For instance, depending upon the relative a:b:c ratios of the polymer, the composition can have a form at ambient temperature of liquid, paste, hydrogel, putty, or solid. Thus, the form of the composition can be controlled, with a preferred form generally depending upon the desired application process and location of the material. For example, a less rigid, paste or hydrogel type of form may be preferred in those embodiments in which the composition is to be delivered in vivo such that the composition can self-conform to the application site following delivery thereto. In other embodiments, however, a more rigid form, such as putty, may be preferred. This may be preferred, for instance, when the material is to be manually formed during application, for example when the material is to be applied over a surface or manually shaped to conform to a void left in a bone following a surgical procedure.

Disclosed polymers are not limited to those materials exhibiting organic solubility, and in other embodiments, a polymer can be derivatized to include functionality to improve the aqueous solubility of the product polymer. For example, a water-soluble polysaccharide, e.g., a water-soluble chitosan, such as O-carboxymethylated chitosan, N-carboxymethyl chitosan or lactose-linked chitosan, can be synthesized according to known methodology. Following initial formation, the water-soluble chitosan can be grafted with crosslinking groups, for instance photocurable groups, such as methacrylate and/or acrylate groups.

An embodiment for a formation process of a water soluble, photocurable chitosan can be illustrated as follows:

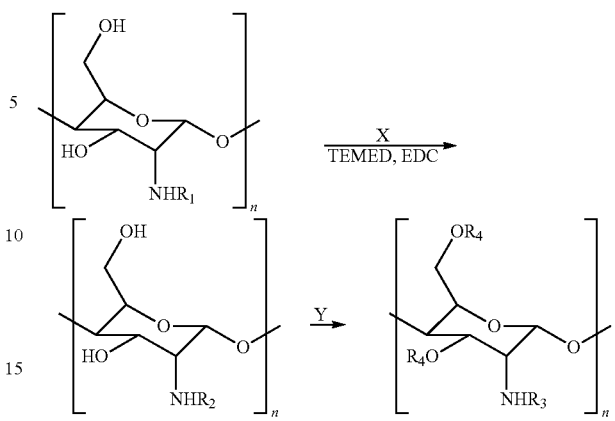

$R_1$=H, OCCH$_3$;
X: Lactobionic acid;

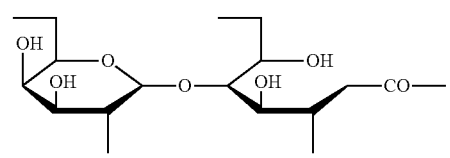

$R_2$=H, OCCH$_3$, X
Y: glycidyl methacrylate

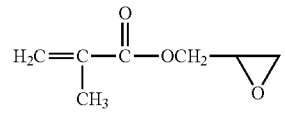

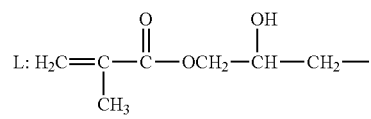

$R_3$=H, OCCH$_3$, X, L
$R_4$=H, L

A water-soluble polysaccharide can be derivatized with photocurable materials other than those of the above scheme. For instance, a water-soluble polysaccharide can be derivatized with PEG-diacrylate, PEG-dimethacrylate and/or PEG-PLA-PEG-dimethacrylate. Such functionalities can be utilized to regulate the degradation rate and mechanical properties of the final crosslinked network, which can broaden its application in biomedical uses.

Disclosed scaffolds can be formed with porosity. For instance, filler can be included in the composition during formation that can be later removed to provide an interconnected porosity in the cured composition. For example, any water soluble salt, sugar, etc. can be added to the composition prior to cure. Following cure, the additive can be leached from the cured matrix to provide an interconnected porosity in the cured product. Additives soluble in an organic solvent can optionally be utilized to introduce porosity. For example, wax particles or spheres can be utilized and then later removed from the matrix with hexane. Any suitable filler can be utilized to provide the desired porosity including, without limitation, organic or aqueous soluble fibers, particles, or the like. Through combination of simple in situ curing and leaching methods, the polymeric network can be used to form porous scaffolds with desired pore size as may be utilized in one embodiment for tissue engineering.

Following formation, the polymeric network can be used as is, for instance in a bone wax application, or can be combined with additional additives such as antibiotics, growth factors, nutrients, drugs, and the like, prior to use.

In one embodiment, a biocompatible strengthening additive can be incorporated into the matrix. For example, disclosed polymeric matrixes can be fabricated with one or more protein additives. For instance, desired proteins can be mixed with the composition prior to cure. The in situ crosslinking process can then entrap the protein into the formed network. The interaction between the polysaccharide backbone (e.g., chitosan) and the protein can affect the morphology of scaffolds as well as the release profile of the proteins from the network.

A protein additive can be either primarily structural or functional in nature. For example, a protein additive that is a structural protein in normal tissue, such as collagen or gelatin, can be incorporated into the polymeric matrix. In such an embodiment, amino acid segments of the protein can provide sites for cell attachments. In addition, a structural protein can regulate the cell behavior, thus increasing the bioactivity of the composition. In addition, a structural protein can enhance the mechanical characteristics of the matrix. For example, gelatin, as may be formed via partial hydrolysis of collagen, can be incorporated into the matrix. The mechanical strength of the matrix can be increased through addition of gelatin. For instance, the storage and loss modulus of a composite can be greater than a matrix including the cured polymer network only.

Proteins that are more actively functional can be incorporated in a polymeric matrix. The presence and/or release of a functional protein from a polymeric network can enhance the function of the scaffold. For example, an osteogenic protein such as bone morphogenic protein 2 (BMP2) can be incorporated into the polymeric matrix. BMP-2 belongs to the TGF-β superfamily of proteins. It plays an important role in the development of bone and cartilage and is involved in the Hedgehog pathway, TGF-beta signaling pathway, and the Cytokine-cytokine receptor interaction. It has been demonstrated to potently induce osteoblast differentiation in a variety of cell types.

Multiple additives can be incorporated into a polymeric matrix. For instance, BMP-2 can be incorporated in a matrix in conjunction with gelatin. The interaction between BMP-2 and gelatin can elongate the retention time of BMP-2 without impacting its bioactivity, thus enhancing characteristics of the scaffolds, e.g., the osteoinductivity of the scaffold. Other primarily functional protein additives can include, without limitation, growth factors, chondrogenic proteins, and the like. Bioactive proteinaceous agents can be incorporated a polymeric matrix following cure according to any standard process, such as, for example, a simple soaking process.

Inorganic additives are also contemplated for disclosed matrices. For example, the phase conversion upon crosslinking can be used to incorporate not only organic bioactive additives such as proteins, but can also enable incorporation of inorganic components, such as bioactive ceramics (e.g., β-TCP or hydroxyapatite powder) and/or other particles. The addition of bioactive inorganic additives, such as bioceramics, can further improve the bone regeneration characteristics of disclosed compositions.

Other additives encompassed by the present disclosure can include other biologically active agents such as, for example, small molecular drugs that can be entrapped in the cured polymeric composite. For example hydrophobic biologically active agents as may be dissolved in an organic solvent such as DMSO can be loaded into a cured matrix through a simple soaking process. Incorporation of drugs, such as antibiotics, and release of the drugs during use can enhance the capability of compositions in preventing infection.

Disclosed materials are not limited to utilization in bone wax applications. It should be understood that disclosed matrices can be utilized in a variety of biomedical applications and can be processed according to multiple techniques. For example, good solubility in organic solvent, photocurability, cytocompatibility and good mechanical properties can make disclosed polysaccharide-based compositions suitable for scaffolding materials formed according to a stereolithography process. Stereolithography is a layer-by-layer scaffold printing process using a computer controlled UV laser. With good spatial and temporal control, scaffolds with desired macro-shape and topography can be printed out for biomedical use.

Disclosed biomaterials can be used in one embodiment as scaffolds in biomedical applications, such as tissue engineering. Beneficially, disclosed polysaccharide-based materials can mimic the environment of the extracellular matrix (ECM), and can provide sites for cell attachment. In addition, scaffolds can provide a location to regulate the differentiation and proliferation of cells loaded onto the scaffolds. According to this embodiment, scaffolds can be seeded with cells through adhesion and cellular migration, seeded cells may, in some embodiments, couple with application of pressure through simple stirring, pulsatile perfusion methods or application of centrifugal force.

The disclosed subject matter may be better understood with reference to the examples that are set forth below. Each example is provided by way of explanation of the information described herein, not as a limitation thereof.

EXAMPLE 1

Formation of a Photocurable, Biocompatible, Polysaccharide-Based Polymer Networks Chitosan with high molecular weight and more than 85% deacetylation, dimethyl sulfoxide (DMSO), methane sulfonic acid, benzoyl chloride, methacryloyl chloride, ammonium hydroxide water solution (5N), and Iragure 2959 (photo-initiator) were obtained from commercial vendors.

A first sample was formed as follows: 1 g chitosan powder (DD=80%) was dissolved in 15 ml methane sulfonic acid and the mixture was stirred until the chitosan was completely dissolved. Acyl chloride at 5 times the molar ratio of the glucosidic unit was added dropwise into the solution over a 30 minute period. The reaction was continued for another 3 hours and the solution was stored at −20° C. overnight. After thawing, the solution was added dropwise into excess water to obtain a precipitate that was then filtered and stirred in 4% amine water solution overnight. The final product was obtained after repeated filtering, rinsing, and vacuum drying over $P_2O_5$ until constant weight was achieved.

In this sample, the acyl chloride mixture used was benzoyl chloride and methacryloyl chloride. The total moles of chloride were 5 times the moles of the glucosidic unit in chitosan. The ratio of benzoyl chloride to methacryloyl chloride was adjusted. Specifically, the ratio of benzoyl chloride to methacryloyl chloride was adjusted to 1:3, 1:1 or 3:1. Respective products were labeled BMC13, BMC11 and BMC31. Photocuring rate varied with degree of substitution (DS) of methacrylate groups. For example, BMC13 cured more quickly than did BMC11, while BMC31 exhibited the slowest curing rate.

The FTIR and NMR characterizations of these materials are shown in FIG. 2 and FIG. 3, respectively. The singular acyl chlorides, benzoyl chloride and methacryloyl chloride, were also used alone in a similar synthesis process to obtain a modified chitosan as a control, which is labeled BC and MC, respectively, on FIGS. 2 and 3.

These photocurable chitosans were found to have very good solubility in common organic solvents, such as DMSO, DMF, DMAC, acetone, etc. This is believed to be due to the high degree of substitution (DS) of benzoyl groups on the chitosan backbone, which is due to the long reaction time and high feeding ratio of acyl chlorides. Methane sulfonic acid cleaves the backbone of the polysaccharide chain, thus decreasing the mechanical properties of the photocured chitosans.

Figure 4:
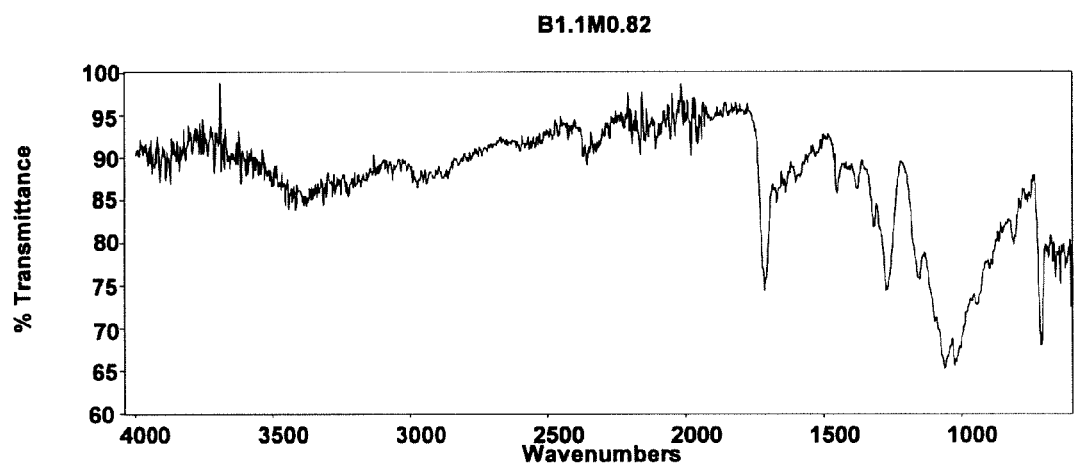
FIG. 4 illustrates the FTIR spectroscopy results of another composition as described herein.
Figure 5:
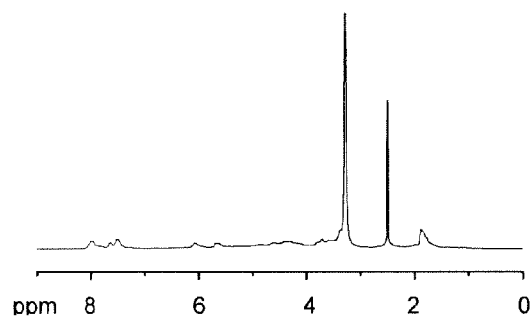
FIG. 5 is the $^1$H-NMR spectra of the composition of FIG. 4.

A second sample was formed as follows: 1 g chitosan powder (DD=80%) was dissolved in 15 ml methane sulfonic acid for 20 minutes. And then 1.10 g benzoyl chloride and 0.82 g methacryloyl chloride were mixed and added dropwise into the solution. After 30 minutes reaction time, the solution was added dropwise to ammonium hydroxide aqueous solution (100 ml 5N ammonium hydroxide+600 ml DI water). The solution was left at room temperature for 1 hour to precipitate the product, and then the precipitation was filtered, washed with DI water several times and dried under vacuum with $P_2O_5$. The final product was labeled B1.1M0.82. The FTIR and NMR for this sample are shown in FIG. 4 and FIG. 5, respectively.

Figure 6:
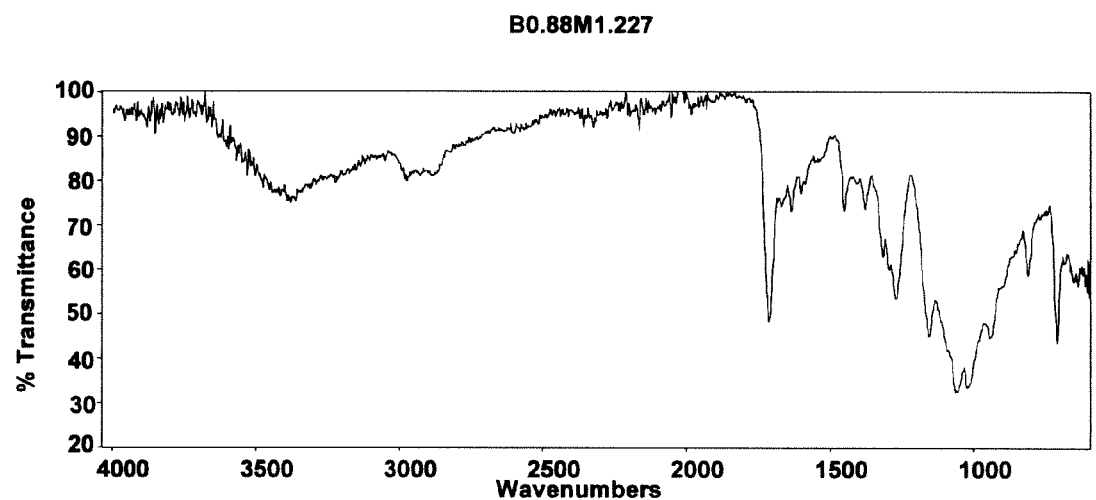
FIG. 6 illustrates the FTIR spectroscopy results of another composition as described herein.
Figure 7:
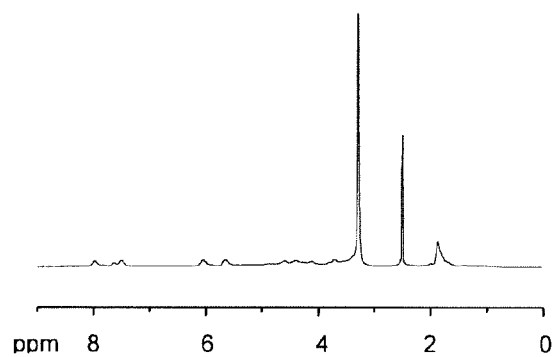
FIG. 7 is the $^1$H-NMR spectra of the composition of FIG. 6.

A third sample was formed as follows: 1 g chitosan powder (DD=80%) was dissolved in 15 ml methane sulfonic acid for 20 minutes. Following, 0.88 g benzoyl chloride and 1.227 g methacryloyl chloride were mixed and added dropwise to the solution. After 30 minutes, the solution was added dropwise to the ammonium hydroxide aqueous solution (100 ml 5N ammonium hydroxide+600 ml DI water). The solution was held at room temperature for 1 hour to precipitate the product, and then the precipitate was filtered, washed with DI water several times and dried under vacuum with $P_2O_5$. The final product was labeled B0.88M1.227. FTIR and NMR for this sample are shown in FIG. 6 and FIG. 7, respectively.

Figure 8:
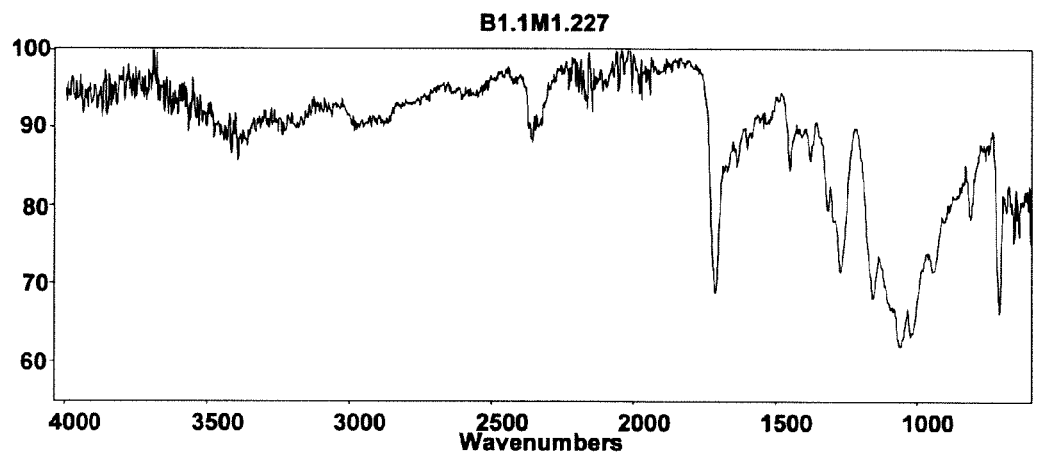
FIG. 8 illustrates the FTIR spectroscopy results of another composition as described herein.
Figure 9:
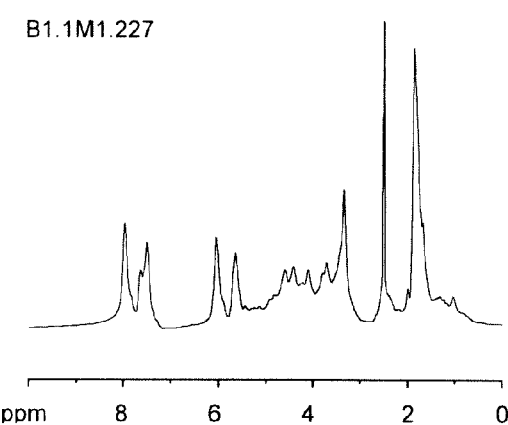
FIG. 9 is the $^1$H-NMR spectra of the composition of FIG. 8.

A fourth sample was formed as follows: 1 g chitosan powder (DD=80%) was dissolved in 15 ml methane sulfonic acid for 20 minutes. Following, 1.10 g benzoyl chloride and 1.227 g methacryloyl chloride were mixed and added dropwise into the solution. Following 30 minutes reaction, the solution was added dropwise to the ammonium hydroxide aqueous solution (100 ml 5N ammonium hydroxide+600 ml DI water). The solution was held at room temperature for 1 hour to precipitate the product, and then the precipitate was filtered, washed with DI water several times and dried under vacuum with $P_2O_5$. The final product was labeled B1.1M1.227. The FTIR and NMR for this sample are shown in FIG. 8 and FIG. 9, respectively.

The samples 2, 3 and 4 photocurable chitosans exhibited good solubility. For instance, the solubility of B1.1M1.227 (sample 4) was higher than B1.1M0.82 (sample 2) and B0.88M1.227 (sample 3), which is due to higher DS of benzoyl groups in B1.1M1.227. B1.1M1.227 can be easily dissolved into DMSO to get a 20% (w/w) solution. For B1.1M0.82 and B0.88M1.227, longer dissolution time is required to obtain a 20% (w/w) solution.

Figure 10:
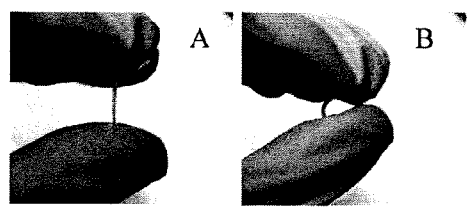
FIG. 10 includes photographs of a photocured chitosan film as described herein prior to (FIG. 10A) and following (FIG. 10B) bending.

The time of reaction will impact the mechanical properties of a photocured chitosan as the methane sulfonic acid is a strong acid which will cleave the backbone of chitosan and decrease the MW of photocurable chitosan with time, thus decreasing the final mechanical properties of the photocured chitosans. Accordingly, in samples 2, 3 and 4, the reaction time was reduced to 30 minutes and the photocurable chitosans were purified directly following 30 minutes reaction, rather than leaving the solution at −20° C. overnight, as was done with sample 1. In addition, the amount of acyl chlorides was reduced in samples 2, 3, and 4 in order to decrease DS while maintaining the solubility and photocurability. The subsequent product was found to have increased mechanical properties as compared to the products of sample 1, though all materials exhibited excellent mechanical characteristics. For example, the photocured chitosans were quite flexible (FIG. 10).

The photocured chitosan films BMC13, BMC11 and BMC31 (sample 1) were sterilized with 70% ethanol for 30 minutes, and then air-dried in a hood. NIH 3T3 fibroblasts were used for cytocompatibility testing. After counting, 5,000 NIH 3T3 fibroblasts were seeded in each well of a 6-well cell culture plate. The sterilized chitosan films were put into the wells and co-cultured with cells. Every other day, Alamar Blue Solution was used to test cytocompatibility. Briefly, after the culture media was removed, 10% v/v Alamar Blue was added and incubated for 4 hours, following which the Alamar Blue Solution was removed and the absorbance was measured at 570 nm and 600 nm. The difference between treated and control cells was calculated and expressed as percentage reduction.

Figure 11:
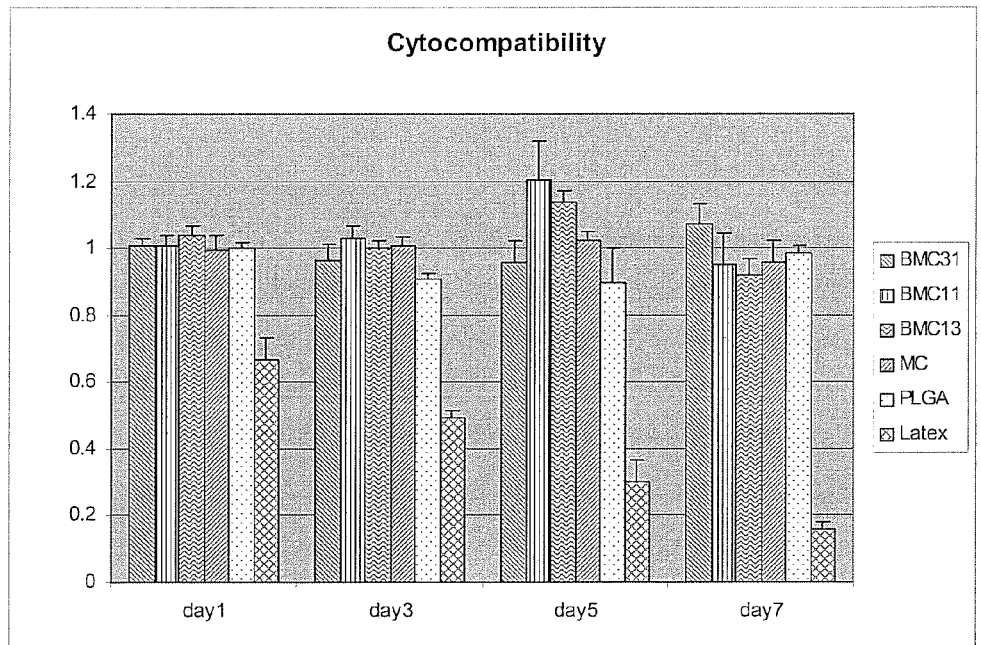
FIG. 11 illustrates the results of cytocompatibility testing of compositions as described herein.

Cytocompatibility results are shown in FIG. 11. The results indicate the photocured chitosan had good cytocompatibility regardless of the DS and the ratio between benzoyl and methacrylate groups.

Figure 12:
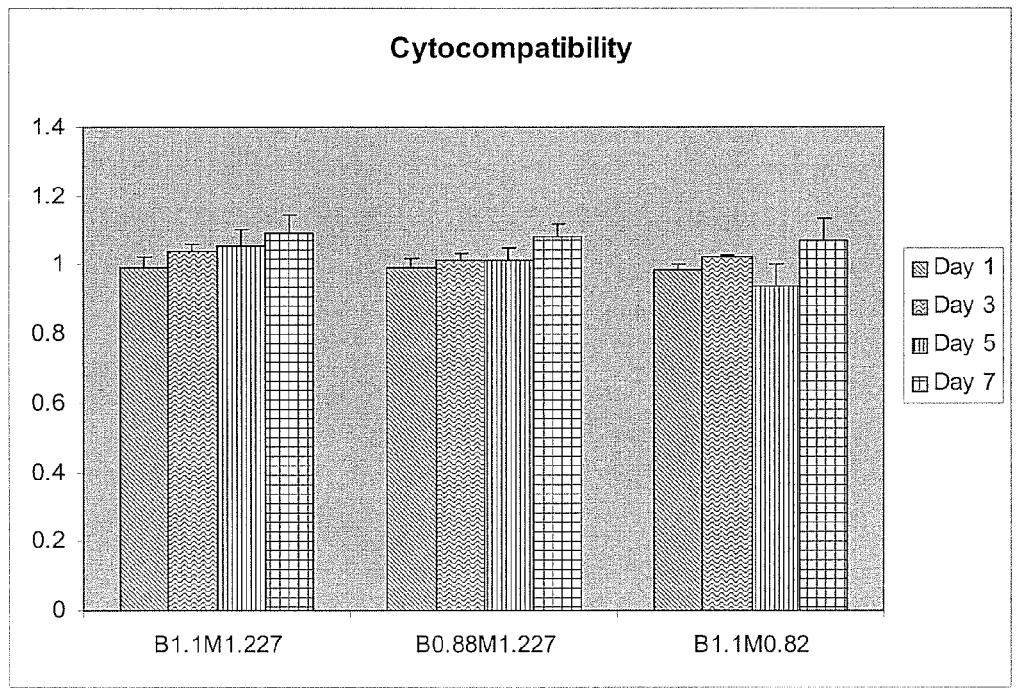
FIG. 12 illustrates the results of cytocompatibility testing of compositions as described herein.

The other samples, B1.1M1.227, B1.1M0.88 and B0.82M1.227 were also photocured on the bottom of a 6 well plate, and fetal bovine osteoblasts were seeded and cultured on the photocured chitosan for 7 days. Cytocompatibility results are shown in FIG. 12. Following the 7 day culture period, the cells were fixed and stained with phaloidin 488 and drag 5 (for the actin and nuclei, respectively). The morphology of the cells was observed by confocal microscopy and shown in FIG. 13 including a control (FIG. 13A, six well plate alone (polystyrene culture plate)), B0.88M1.227 (FIG. 13B), B1.1M0.82 (FIG. 13C), and B1.1M1.227 (FIG. 13D). As can be seen, the photocurable chitosan with different DS has different influence on osteoblast spreading. In particular, Osteoblasts were seen to spread very well on B1.1M1.227, while they did not spread very well on B1.1M0.88 or B0.88M1.227.

EXAMPLE 2

A PLGA composition [Birmingham Polymers Inc., Birmingham, Ala. USA, 50:50 ratio, MW 53,000 Da] was compared to a polysaccharide-based polymer as disclosed herein for in vitro biocompatibility comparisons.

The polysaccharide had a general structure of:

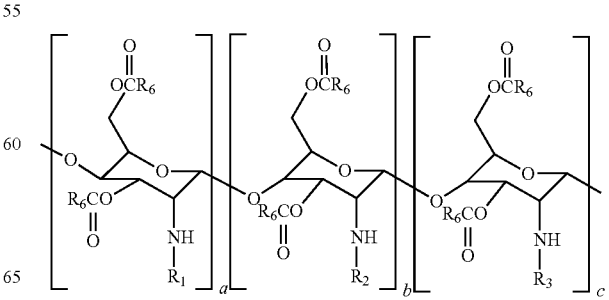

in which
(a+b):c=85%:15%, and a:b=1:9,
in a $R_1$=PEG-diols (200 g/mol),
in b $R_2$=PCL-dials (530 g/mol),
in c $R_3$=chitosan The PLGA material and the polysaccharide-based composition were loaded with human osteoblast cells (hFOB 1.19, ATCC; Manassas, Va., USA) and observed over time.

Figure 14:
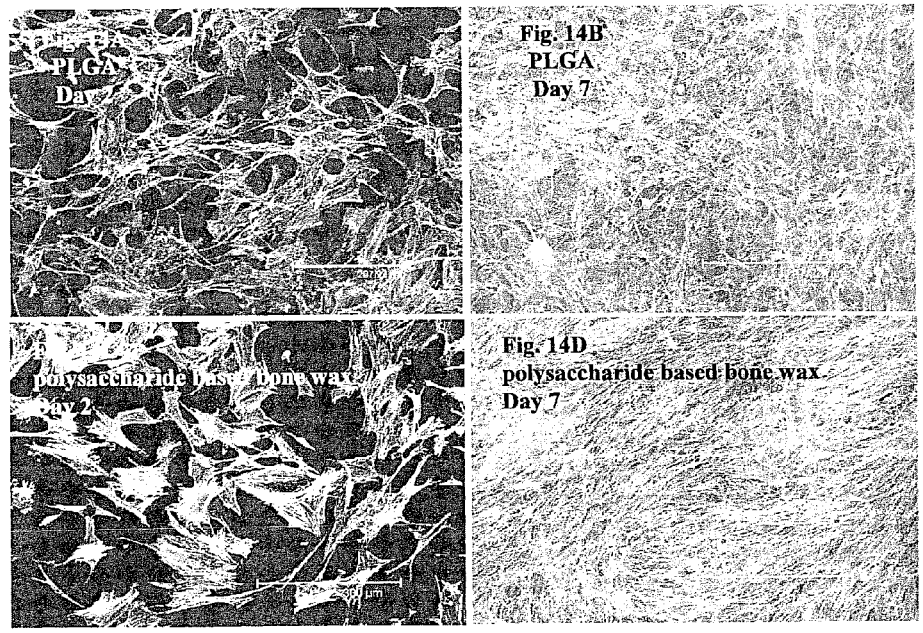
FIG. 14 compares the biocompatibility of osteoblasts cultured on a composition as herein (disclosed FIGS. 14A and 14B) with that of osteoblasts cultured on a poly (L-lactide-co-glycolic acid) (PLGA) composition (FIGS. 14C and 14D)

FIG. 14 illustrates the results. As can be seen, by day 7, the matrix of the polysaccharide-based composition has developed a more uniform consistency, with large numbers of surviving osteoblasts fairly evenly distributed throughout the matrix.

Figure 15:
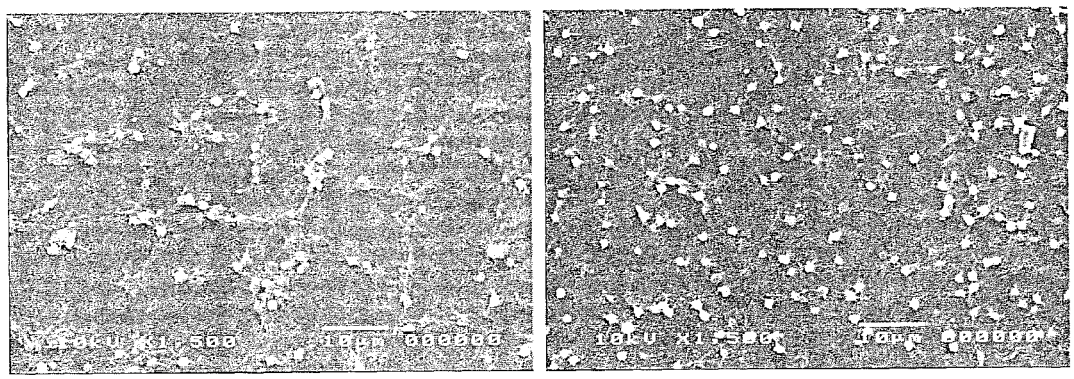
FIG. 15 compares the thrombogenic activity of a composition as herein disclosed (FIG. 15B) as compared to that of a PLGA composition (FIG. 15A)

To compare thrombogenic characteristics of the materials, $1 \times 10^5$ platelets/4 of platelet testing solution was obtained from whole blood of New Zealand White rabbits. 0.7 ml prepared platelet testing solution was applied on the samples for 30 minutes at 37° C. The films were washed three times with mild shaking in 0.1 M PBS to remove non-adherent platelets. Following, the samples were fixed with freshly prepared 2.5% glutaraldehyde for 20 min. After washing with 0.1 M PBS again, the samples were dehydrated in an ethanol-graded series (50, 60, 70, 80, 95 and 100%) for 10 minutes each and allowed to dry at room temperature. The platelet-attached surfaces were gold deposited in vacuum and visualized using SEM. FIG. 15 illustrates the relative in vitro thrombogenic activity of the PLGA material (FIG. 15A) with that of the polysaccharide-based composition (FIG. 15B).

EXAMPLE 3

Sternotomies were performed on test subjects. FIG. 16A is an x-ray image of a typical subject 42 days post-surgery that included application of a conventional beeswax-based bone wax to the sternal sections. FIG. 16B is a similar image of a test subject to which a polysaccharide-based bone wax as described above in Example 2 was applied. As can be seen with reference to FIG. 16, in the beeswax group, bone regeneration at the bone wax applied region (middle part of the sternum) was inhibited. In the polysaccharide-based bone wax group, the halves of sternum were reunited together.

Six weeks post-procedure, sternal sections were examined. FIG. 17 illustrates the osteoconductivity comparison of the two materials, with the beeswax-based bone wax on the left (FIG. 17A), and the polysaccharide-based bone wax shown on the right (FIG. 17B). Both materials were implanted into nude mice subcutaneously seeded with bovine osteoblasts for 6 weeks. HE staining showed bone and fibrous tissue. As can be seen with reference to the FIG. 17, more bone tissue formed in polysaccharide-based composition.

Figure 18B:
Figure 18C:
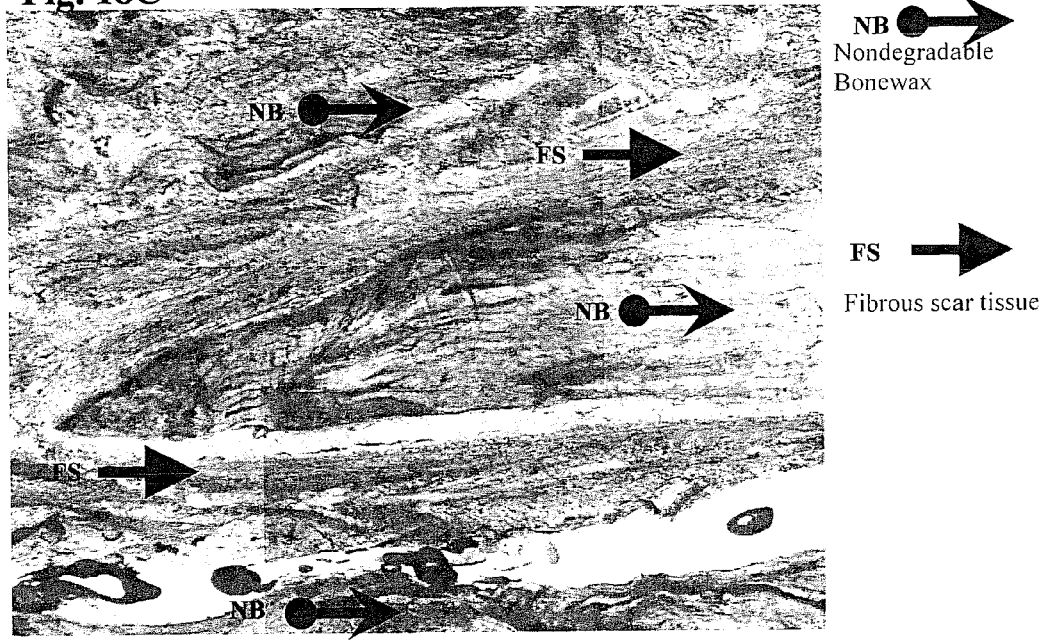
Figure 18D:
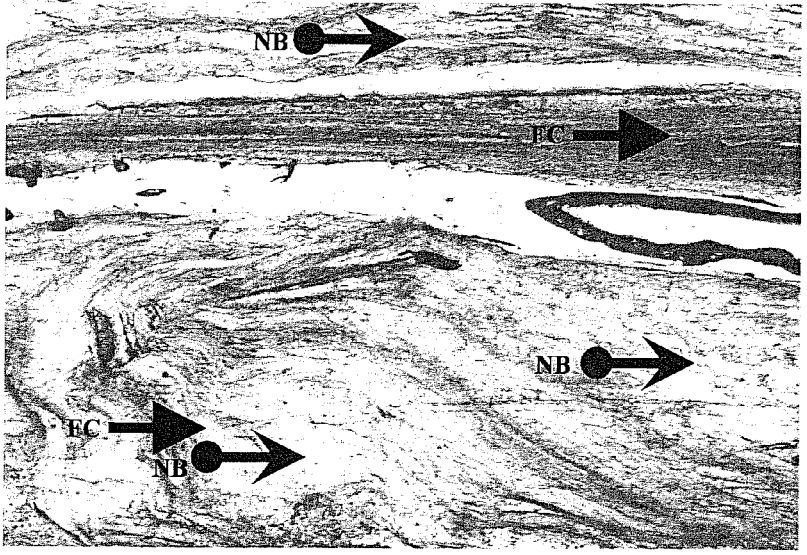
Figure 18E:
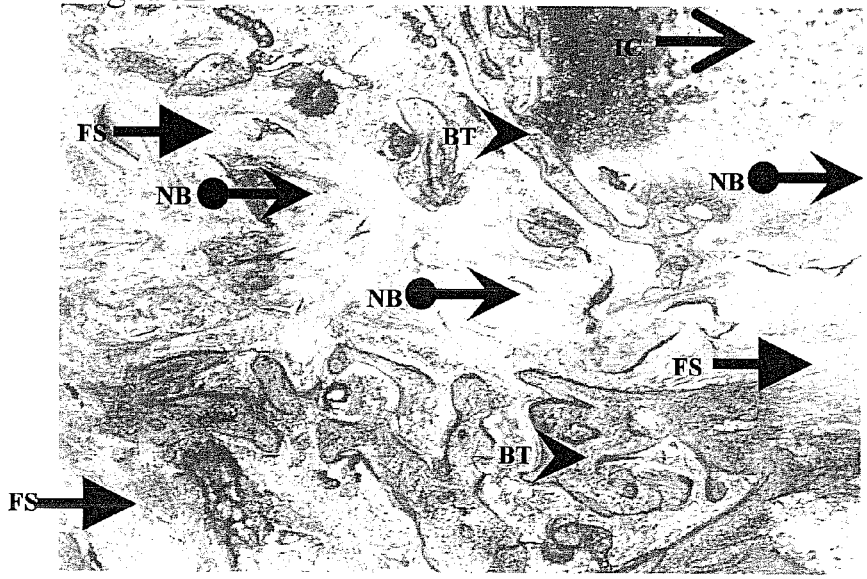

FIG. 18A illustrates a typical bone wax implantation zone of the subject of FIG. 16A including the beeswax-based bone wax. The sections of FIG. 18A that are marked 18B, 18C, 18D, and 18E correspond to the Figures of the same numbers. As can be seen in FIGS. 18B-18E, patches of the non-degradable bone wax are surrounded by fibrous scar tissue throughout the zone.

Figure 19A:
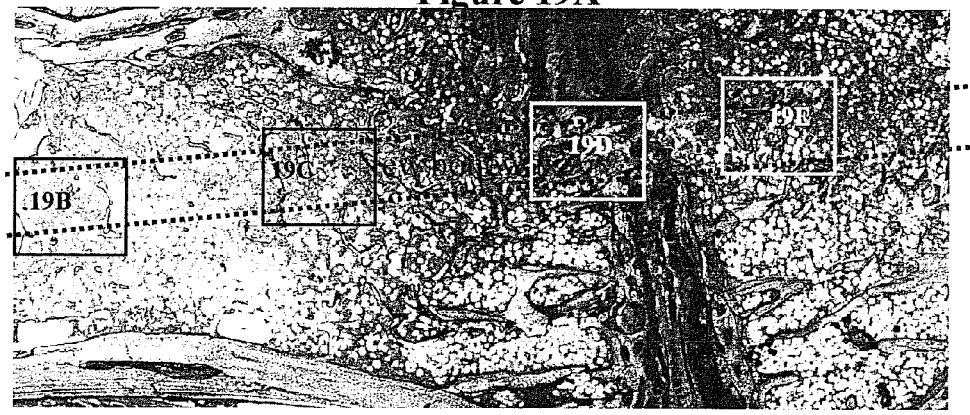
FIG. 19A is an image of a sternal section of the specimen of FIG. 16B including a bone wax implantation zone of a bone wax composition as herein disclosed.
Figure 19B:
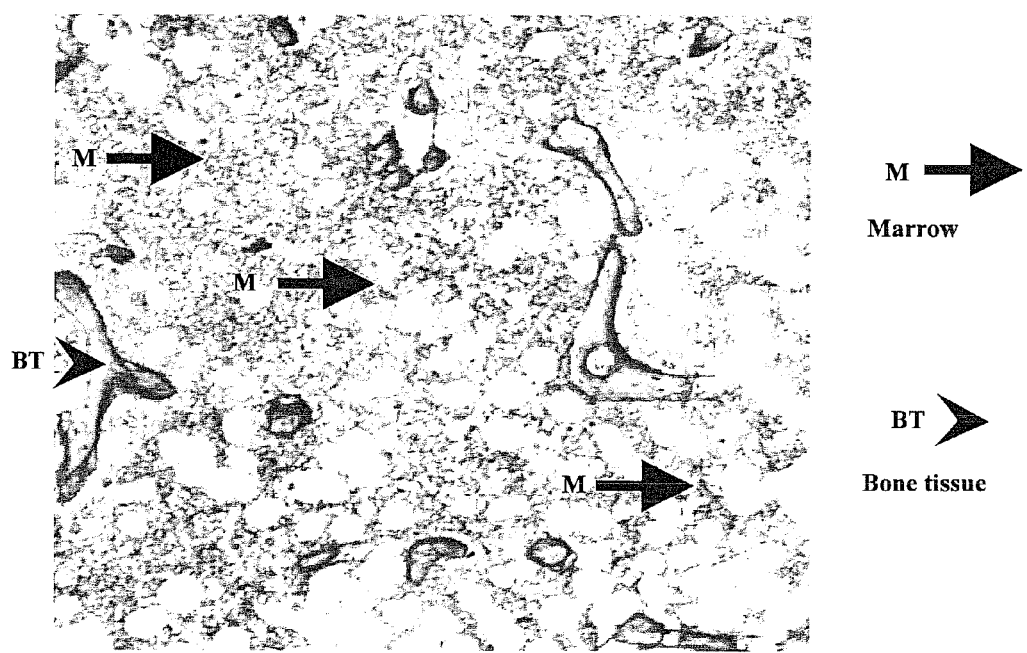
FIGS. 19B-19E are images of portions of FIG. 19A.
Figure 19C:
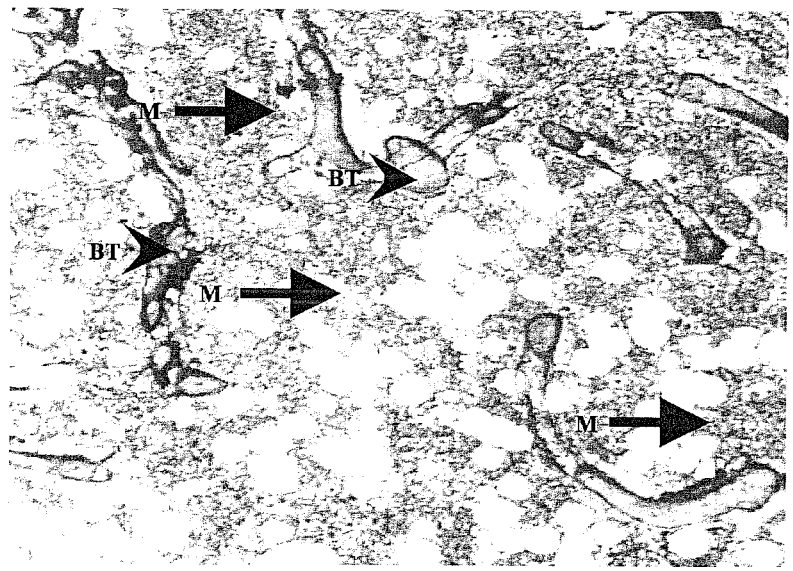
Figure 19D:
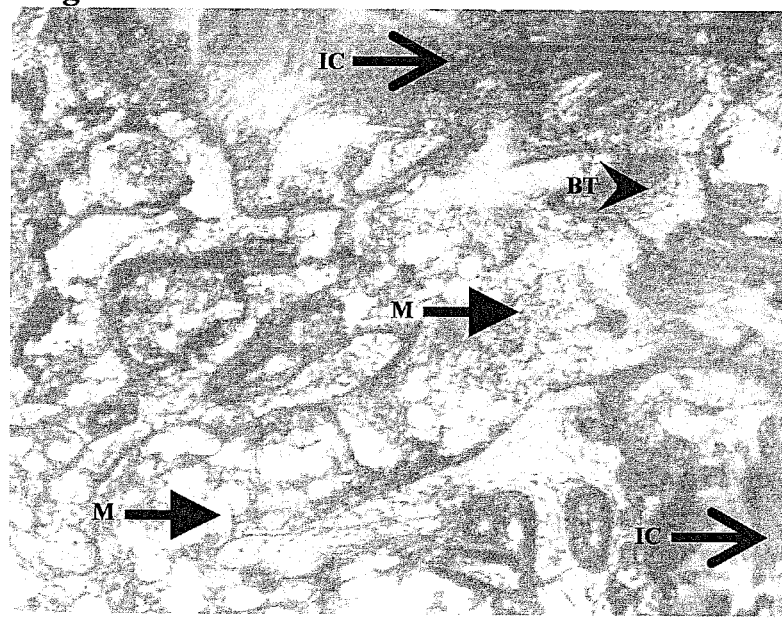
Figure 19E:
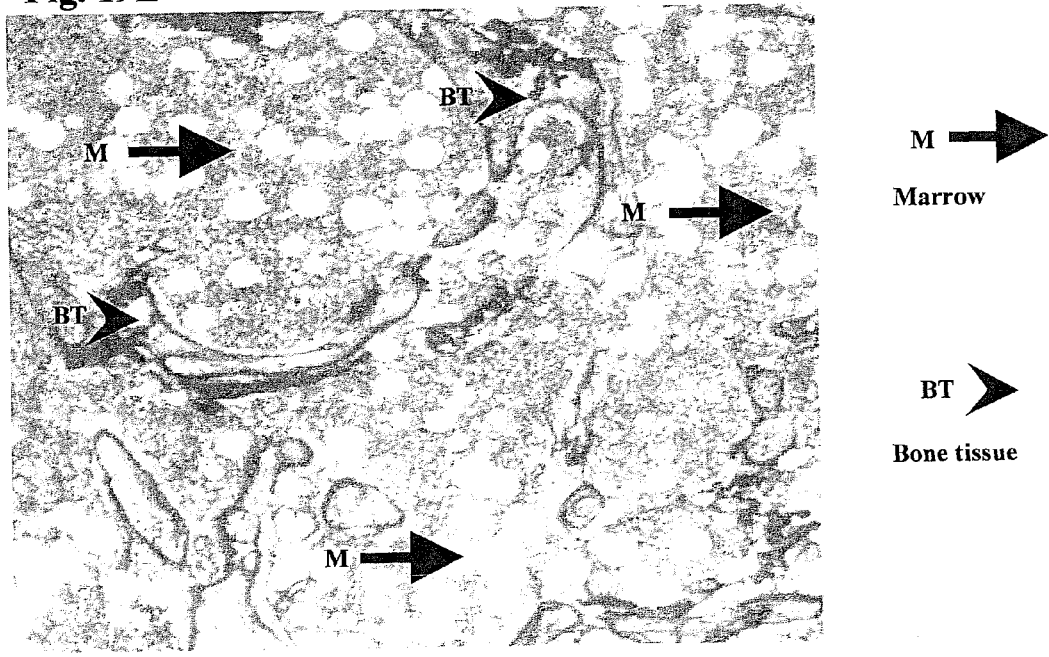

FIG. 19A illustrates a similar implantation zone but for a subject to which the polysaccharide-based bone wax was applied (FIG. 16B). The sections of FIG. 19A that are marked 19B, 19C, 19D, and 19E correspond to the Figures of the same numbers. As can be seen in these figures, the zone includes large amounts of marrow and bone tissue with no visible fibrous scar tissue in the zone.

EXAMPLE 4

A first sample was formed as follows: 4.52 g L-lysine diisocyanate (LDI) (0.02 moles) was added to a three-neck flask with small amount of anhydrous DMF. 0.05 g Dibutyltin dilaurate and 5.3 g PCL-diol (Mn=530, 0.01 mole) were then added into the flask. The flask was kept in 80° C. oil bath and allowed to react for 1 hour with mechanical stirring. Following, 0.46 grams anhydrous ethanol with 20 ml anhydrous DMF was added to the flask and allowed to react for another 1 hour. 1.5 g benzoylated chitosan (BC) was dissolved into 10 ml anhydrous DMF and added dropwise into the flask following the second reaction period. The reaction was carried out at 80° C. for 4 hours. After reaction, the solution was dropped into excess water to precipitate the product. The product was washed with DI water several times and dried under vacuum with $P_2O_5$.

A second sample was formed as follows: 4.52 g LDI (0.02 moles) was added to three-neck flask with small amount of anhydrous DMF. 0.05 g Dibutyltin dilaurate and 12.5 g PCL-diol (Mn=1250, 0.01 mole) were then added to the flask. The flask was kept in an 80° C. oil bath and allowed to react for 1 hour with mechanical stirring. Following, 0.46 g anhydrous ethanol with 20 ml anhydrous DMF was added into the flask and reaction was allowed to proceed for another 1 hour. 1.5 g benzoylated chitosan (BC) was dissolved into 10 ml anhydrous DMF and added dropwise into the flask. The reaction was carried out at 80° C. for 4 hours. After reaction, the solution was dropped into excess water to precipitate the product. The product was washed with DI water several times and dried under vacuum with $P_2O_5$.

A third sample was formed as follows: 4.52 g LDI (0.02 moles) was added to three-neck flask with small amount of anhydrous DMF. 0.05 g Dibutyltin dilaurate and 5.3 g PCL-diol (Mn=530, 0.01 mole) were then added into the flask. The flask was kept in an 80° C. oil bath and allowed to react for 1 hour with mechanical stirring. Following, 1.018 g glycidyl methacrylate with 20 ml anhydrous DMF was added into the flask and reaction was allowed to proceed for another 1 hour. 1.5 g benzoylated chitosan (BC) was dissolved into 10 ml anhydrous DMF and added dropwise into the flask. The reaction was carried out at 80° C. for 4 hours. After reaction, the solution was dropped into excess water to precipitate the product. The product was washed with DI water several times and dried under vacuum with $P_2O_5$.

EXAMPLE 5

Porous discs as may be utilized for bone tissue engineering were fabricated from photocurable chitosans. A height-adjustable mold was used. A high MW poly(ethylene) (PE) block was drilled with a cylindrical hole having a diameter of 8 mm. A poly(tetrafluoroethylene) (PTFE) pole with diameter in 8 mm was inserted into the cylindrical hole to make the height-adjustable mold. When fabricating porous discs, the height was adjusted to 2 mm, and sodium chloride having a 200-300 μm size range was poured into the mold. A photocurable chitosan solution was then poured over the salts. Three different solutions were used to form three different porous discs. Specifically, BMC13, BMC11, and BMC13, as described in Example 1, above, were utilized. The solution penetrated to the bottom and filled the interspaces between salts. The entire mold was exposed to ultraviolet light for 2 minutes to cure the scaffold. Following cure, the disc was pushed out of the mold and immersed into water to wash off the salts and DMSO. The porous discs were then freeze-dried and the morphology of the porous discs were observed by SEM and shown in FIG. 20 including discs formed of BMC13 (FIG. 20A), BMC11 (FIG. 20B), and BMC31 (FIG. 20C).

To test the osteoconductivity of the porous photocured scaffolds, an in vivo test was developed. The porous disc scaffolds were freeze-dried and sterilized with ethylene oxide. Porous PLGA discs were used as a control. Primary fetal bovine osteoblasts were propagated in monolayer culture until confluence. The harvested cells were then loaded onto porous disc scaffolds at a concentration of at least $5\times10^6$ cells/scaffold. Under general anesthesia and sterile conditions, the porous discs were subcutaneously implanted into the backs of 4-6 week old male, athymic (nu/nu) mice. Six mice were used for each sample type. After 6 weeks, the mice were sacrificed and the implants were harvested. Each explant was processed for paraffin histology and stained with H&E. Results are shown in FIGS. 21A-21D, specifically, BMC13 (FIG. 21A), BMC11 (FIG. 21B), BMC31 (FIG. 21C) and PLGA (FIG. 21D). The reference bar in the images is 200 µm.

Figure 22:
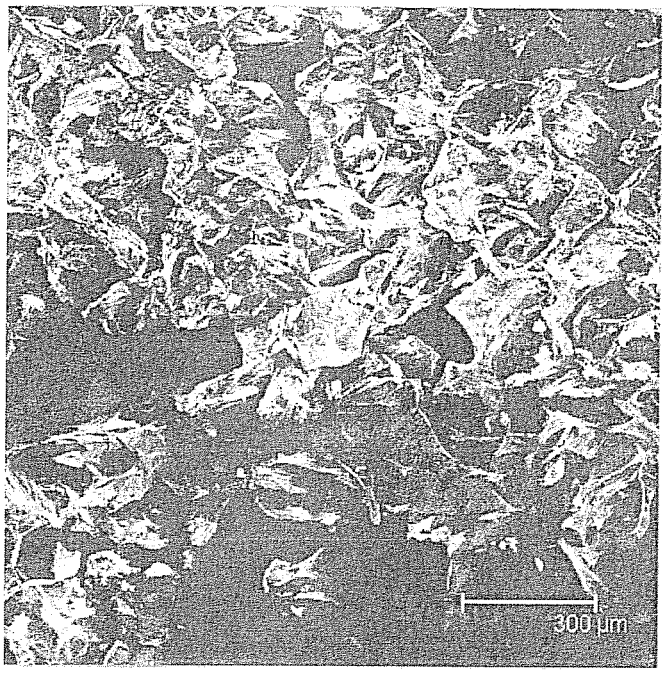
FIG. 22 is an image of a 2 day osteoblast culture in a porous disc as described herein.

Porous discs were also made from B1.1M1.227 of Example 1. Primary fetal bovine osteoblasts were seeded into these pre-wetted discs with a cell density of $1\times10^5$ cells/scaffold. The osteoblast-seeded porous discs were cultured for 2 days, and then the scaffolds were fixed and stained with phalloidin 488 and drag 5 for actin and nuclei. The morphology of the osteoblast cultured on the B1.1M1.227 3-D porous discs were recorded by confocal microscopy and shown in FIG. 22.

EXAMPLE 6

Gelatin was dissolved into DMSO to attain a 5% (w/w) solution. Following an appropriate amount of B1.1M1.227 (formed as described above in Example 1), DMSO or PEG-diacrylate (PEG-DA, MW=750) were dissolved into a gelatin-DMSO solution to form the following solutions:
  a) 5% B1.1M1.227-5% gelatin
  b) 7.5% B1.1M1.227-5% gelatin
  c) 10% B1.1M1.227-5% gelatin
  d) 5% B1.1M1.227-2.5% gelatin
  e) 5% B1.1M1.227-1.25% gelatin
  f) 5% B1.1M1.227-5% gelatin-1% PEG
  g) 5% B1.1M1.227-5% gelatin-2.5% PEG
  h) 5% B1.1M1.227-5% gelatin-5% PEG solution Appropriate amount of photoinitiator, Iragure 2959, was also added to each solution (0.05%). Upon addition of the photoinitiator, each solution was instantly photocured to form a scaffold (discs with 8 mm diameter and 2 mm height or 5 mm height).

Figure 23:
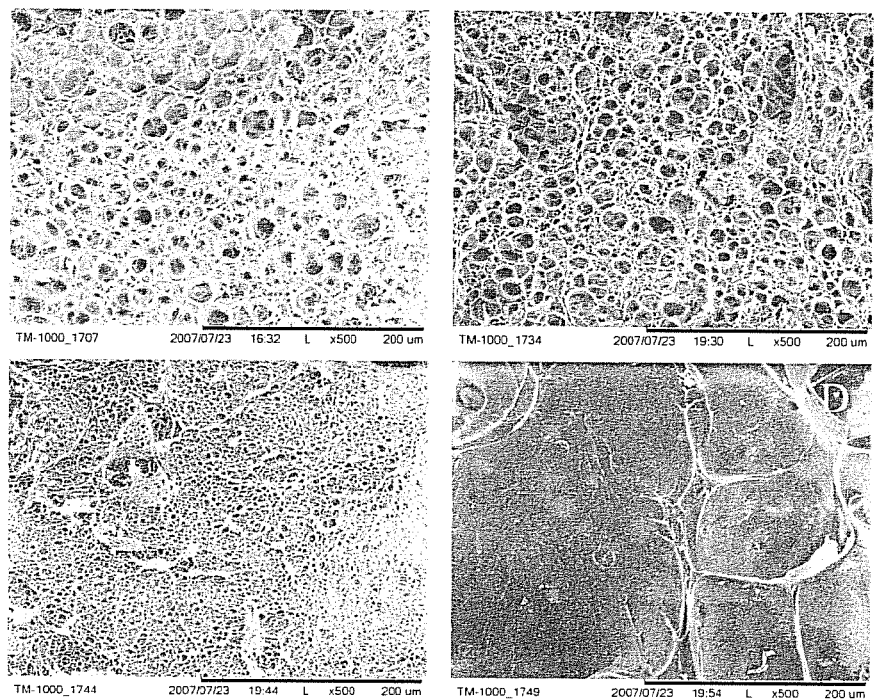
FIGS. 23A-D are scanning electron micrographs (SEM) of photocured discs including a gelatin additive as described herein.
Figure 25A:
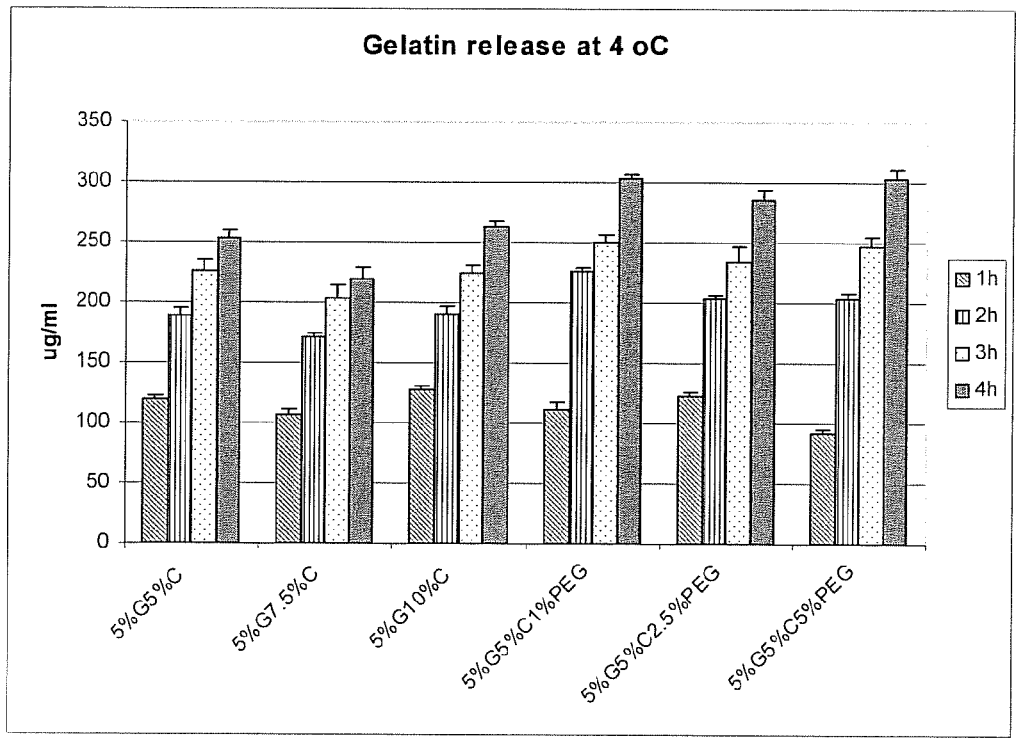
FIGS. 25A and 25B illustrate gelatin release over time at 4° C.
Figure 25B:
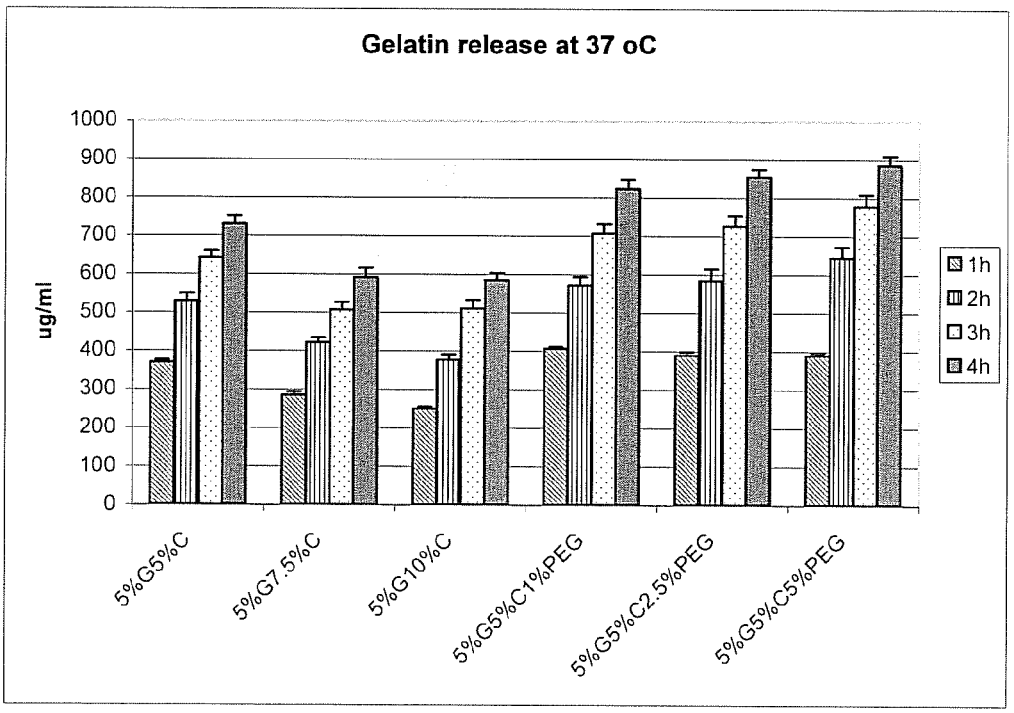

Samples of the 5% B1.1M1.227-5% gelatin solution (a) were photocured to form porous discs with 8 mm diameter and 2 mm height immediately following solution preparation, as well as 4, 8 and 12 hours following solution preparation as described above in Example 4. These discs were frozen-dried and SEM images were taken to examine their morphology. Results are shown in FIG. 23 including FIG. 23A (immediate curing), 23B (4 hour delay prior to cure), 23C (8 hour delay prior to cure), 23D (12 hour delay prior to cure).

SEM images indicated that the micropores formed in the discs reduced in size over time when the solution was held at room temperature before photocuring. The pores of the discs photocured immediately following solution preparation were between about 50 and about 70 µm in diameter. However, the micropores almost disappeared after sitting at room temperature for 24 hours before photocuring (not shown). This is believed to be due to the difference in hydrophobicity between gelatin and B1.1M1.227. Immediately following mixing, the solution tends to phase separation, and immediate photocuring fixes this phase separation. As such, and as can be seen in FIG. 23A, the pores can be visualized. However, when placed at room temperature for several hours, the gelatin in DMSO tends to change its conformation leading to elimination of this phase separation. This conformation adjustment is almost complete after being held at room temperature for 12 hours, which is proved by SEM (FIG. 23D).

A rheology study (frequency sweep from 0.01 Hz to 100 Hz, with constant 0.1% stain) was performed on 8 mm diameter and 5 mm height 5% B1.1M1.227-5% gelatin discs (FIG. 24A) and on 5% B1.1M1.227 discs (FIG. 24B) at room temperature and at 40° C. to measure the visco-elasticity of the discs and the influence of temperature.

The gelatin release at different temperatures (4° C. and 37° C.) from the discs with 8 mm diameter and 2 mm height consisting of different concentration and different co-photocuring molecules was measured over a 4 hour period. Results are shown in FIGS. 24A (4° C.) and 24B (37° C.). As can be seen, the release of gelatin from the composite discs at 4° C. showed no significant differences among the discs formed from different components. The release rate was increased by a factor of about 3 at 37° C. Discs with higher B1.1M1.227 content had lower gelatin release rates due to the denser network structure. However, the addition of PEG-DA co-photocrosslinker into the composite discs conversely increased the gelatin release, which was due to the higher hydrophilicity of PEG and lower interaction with gelatin.

Figure 26:
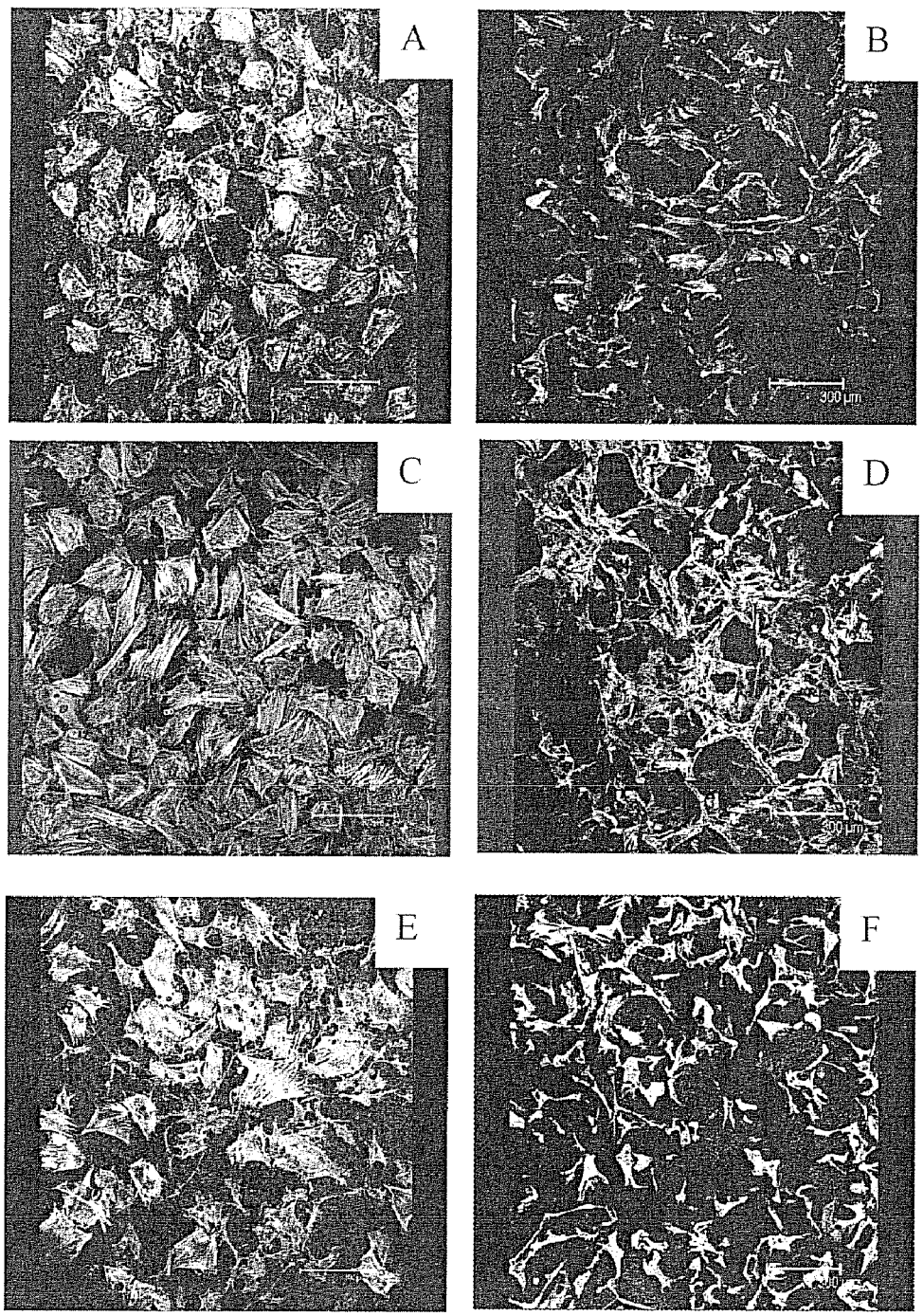
FIGS. 26A-26F illustrate morphology of osteoblasts cultured on films and 3-D porous discs of compositions as described herein.

Osteoblast attachment in 2-D films and 3-D porous scaffolds were examined following the methods described above. For 2-D films, 7 day cultures were taken and for 3-D porous scaffolds, the cells were cultured for 48 hours. The morphology of attached osteoblasts are shown in FIG. 26 including FIG. 26A, showing the morphology of osteoblasts cultured on a film of 5% B1.1M1.227-5% gelatin; FIG. 26B, osteoblasts cultured on a 3-D porous scaffold of 5% B1.1M1.227-5% gelatin; FIG. 26C, osteoblasts cultured on a film of 7.5% B1.1M1.227-5% gelatin; FIG. 26D, osteoblasts cultured on a 3-D porous scaffold of 7.5% B1.1M1.227-5% gelatin; FIG. 26E, osteoblasts cultured on a film of 10% B1.1M1.227-5% gelatin; and FIG. 26F, osteoblasts cultured on a 3-D porous scaffold of 10% B1.1M1.227-5% gelatin.

EXAMPLE 7

Figure 27:
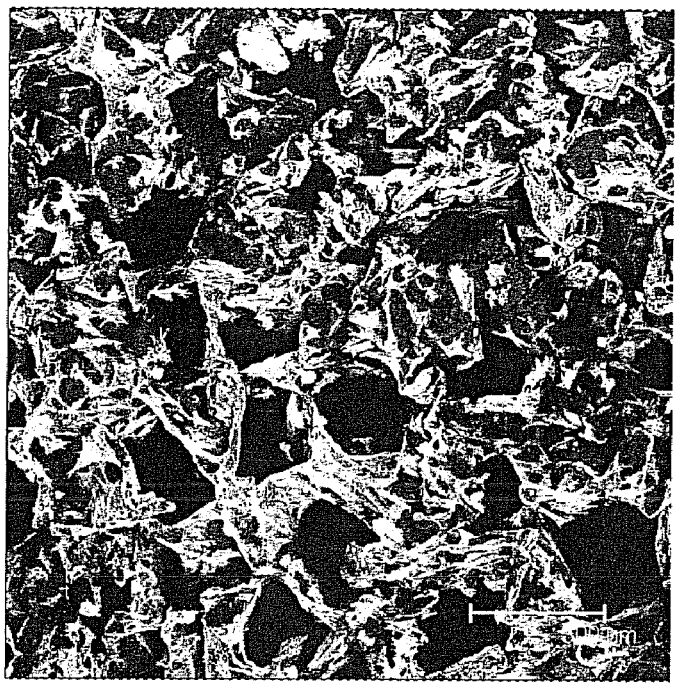
FIG. 27 illustrates the morphology of osteoblasts cultured on a 3-D porous disc of a photocured composite as described herein.

B1.1M1.227 as described above in Example 1 was dissolved into DMSO to form a 20% (w/w) solution. Following, an appropriate amount of β-TCP was added into the solution and stirred to homogenize this mixture. After addition of photo-initiator, the mixture was photocured under UV to form a 3-D porous disc according to methods described above in Example 5. A 2-day fetal bovine osteoblast culture on the porous 3-D scaffolds was examined as previously described. The cells were fixed, stained and observed with confocal microscopy. The morphology of the cells is shown in FIG. 27.

Figure 28:
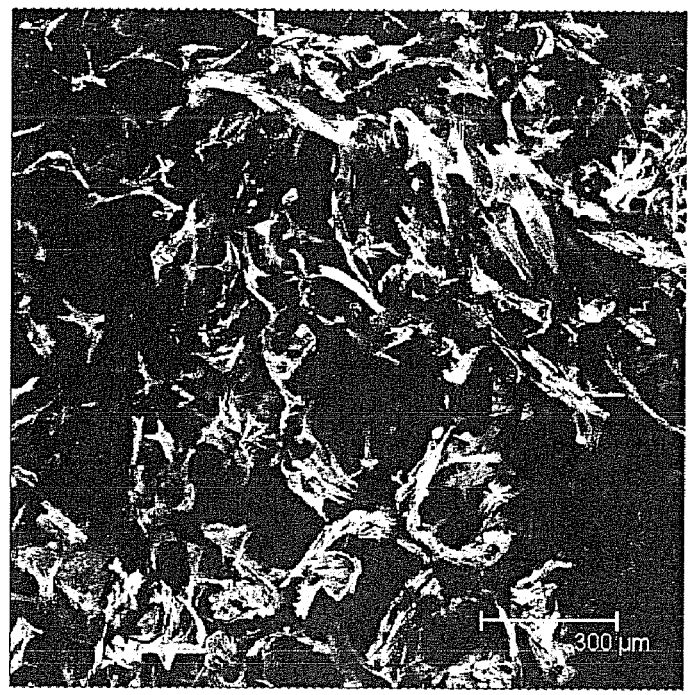
FIG. 28 illustrates the morphology of osteoblasts cultured on a 3-D porous disc of a photocured composite as described herein.

An appropriate amount of β-TCP was also blended into 7.5% B1.1M1.227-5% gelatin solution, as described above in Example 6, and the mixture was photocured under UV to form a 3-D porous disc. A 2-day fetal bovine osteoblast culture in the porous 3-D scaffolds was carried out and examined as previously described. The cells were fixed, stained and observed with confocal microscopy. The morphology of the cells was shown in FIG. 28.

EXAMPLE 8

A water soluble chitosan-based polymeric network was formed according to the following process:
Step 1: Synthesis of lactose-linked chitosan. Chitosan (125 g) was added to 3 L (pH=4.75) of 50 mM TEMED (N,N,N8, N8-tetramethylethylenediamine) containing 56.25 mL concentrated HCl. Following, EDC [32.5 g, 1-ethyl-3-(3-dimethylaminopropyl)carbodiimide] and 4-O-β-D-galactopyranosyl-(1,4)-D-gluconic acid20 (0.25 g of lactobionic acid) were added. This mixture was stirred at room temperature for 24 h, followed by ultrafiltration with a filtration membrane passing unreacted substances below 10 kDa. A powder of lactose-linked chitosan (CH-LA) was obtained by freeze drying.

Step 2: Graft of photocurable groups. 1% w/v solution of CH-LA in distilled water was treated with a 6-, 10-, or 20-fold molar excess of glycidyl methacrylate in the presence of excess triethylamine and tetrabutyl ammonium bromide overnight at room temperature, followed by a 1-h incubation at 60° C. After the reaction, the solution was precipitated in acetone (20 times the volume of the reaction solution) and dissolved in distilled water twice to remove excess reactants. The photocurable chitosan solution was lyophilized and stored desiccated at 4° C.

Although only a few exemplary embodiments have been described in detail above, those skilled in the art will readily appreciate that many modifications are possible in the exemplary embodiments without materially departing from the novel teachings and advantages of this invention. Accordingly, all such modifications are intended to be included within the scope of this invention that is defined in the following claims and all equivalents thereto. Further, it is recognized that many embodiments may be conceived that do not achieve all of the advantages of some embodiments, yet the absence of a particular advantage shall not be construed to necessarily mean that such an embodiment is outside the scope of the present invention.

What is claimed is:

1. A biocompatible composition comprising an osteogenic polymeric matrix including a crosslinked polymer, the polymer having a polysaccharide backbone, the polysaccharide backbone being crosslinked with a first functional group grafted to the polysaccharide backbone, the polysaccharide backbone further comprising a second functional group pendant to the polysaccharide backbone that improves the solubility of the polysaccharide in a solvent, the polymeric matrix further comprising a third functional group grafted to the polysaccharide backbone, wherein the third functional group comprises the reaction product of a polyol and a diisocyanate.

2. The biocompatible composition of claim 1, wherein the polysaccharide is a chitosan.

3. The biocompatible composition of claim 1, wherein the first functional group is a photocurable crosslinking group.

4. The biocompatible composition of claim 1, wherein the solvent is an organic solvent.

5. The biocompatible composition of claim 1, wherein the solvent in an aqueous solvent.

6. The biocompatible composition of claim 1, wherein the matrix defines an interconnected porosity.

7. The biocompatible composition of claim 1, the composition further comprising an additive incorporated within the polymeric matrix.

8. The biocompatible composition of claim 7, wherein the additive is a protein.

9. The biocompatible composition of claim 8, wherein the protein is an osteogenic protein, a growth factor, or a chondrogenic protein.

10. The biocompatible composition of claim 7, wherein the additive is a biologically active additive.

11. The biocompatible composition of claim 1, wherein the composition is osteoinductive.

12. The biocompatible composition of claim 1, wherein the composition is a cellular scaffold.

13. A biodegradable bone wax comprising an osteogenic polymeric matrix including a crosslinked polymer, the polymer having a chitosan backbone, the polymer being crosslinked with a first functional group grafted to the chitosan backbone according to a reaction between a first hydroxyl group of the chitosan backbone and a first acyl chloride such that the first functional group is bonded to the chitosan backbone via an ester linkage, the chitosan backbone further comprising a second functional group pendant to the chitosan backbone that improves the solubility of the polymer in a solvent, the second functional group being grafted to the chitosan backbone according to a reaction between a second hydroxyl group of the chitosan backbone and a second acyl chloride such that the second functional group is bonded to the chitosan backbone via an ester linkage, the chitosan backbone further comprising a third functional group grafted to the chitosan backbone.

14. The biodegradable bone wax of claim 13, wherein the bone wax is osteoinductive.

15. The biodegradable bone wax of claim 13, wherein the bone wax is photocurable.

16. A biocompatible composition comprising an osteogenic polymeric matrix including a crosslinked polymer, the polymer having a chitosan backbone, the polymer being crosslinked with a first functional group grafted to the chitosan backbone according to a reaction between a first hydroxyl group of the chitosan backbone and a first acyl chloride such that the first functional group is bonded to the chitosan backbone via an ester linkage, the chitosan backbone further comprising a second functional group pendant to the chitosan backbone that improves the solubility of the polymer in a solvent, the second functional group being grafted to the chitosan backbone according to a reaction between a second hydroxyl group of the chitosan backbone and a second acyl chloride such that the second functional group is bonded to the chitosan backbone via an ester linkage.

17. The biocompatible composition of claim 16, wherein the polymeric matrix further comprises a third functional group grafted to the chitosan backbone.

18. The biocompatible composition of claim 17, wherein the third functional group comprises the reaction product of a diol or a polyol and a diisocyanate.

19. The biocompatible composition of claim 16, wherein the first functional group is a photocurable crosslinking group.

20. The biocompatible composition of claim 16, wherein the solvent is an organic solvent or an aqueous solvent.

21. The biocompatible composition of claim 16, wherein the matrix defines an interconnected porosity.

22. The biocompatible composition of claim 16, the composition further comprising an additive incorporated within the polymeric matrix.

23. The biocompatible composition of claim 16, wherein the composition is osteoinductive.

24. The biocompatible composition of claim 16, wherein the composition is a cellular scaffold.

* * * * *

UNITED STATES PATENT AND TRADEMARK OFFICE
CERTIFICATE OF CORRECTION

PATENT NO.        : 7,914,819 B1                                          Page 1 of 1
APPLICATION NO.   : 11/875436
DATED             : March 29, 2011
INVENTOR(S)       : Wen et al.

It is certified that error appears in the above-identified patent and that said Letters Patent is hereby corrected as shown below:

Column 13, Line 2 "(a÷b)c..." should read --(a+b)c...--

Signed and Sealed this
Third Day of April, 2012

David J. Kappos
*Director of the United States Patent and Trademark Office*